US011685956B2

(12) United States Patent
Lidgard et al.

(10) Patent No.: US 11,685,956 B2
(45) Date of Patent: *Jun. 27, 2023

(54) METHYLATION ASSAY

(71) Applicant: Exact Sciences Corporation, Madison, WI (US)

(72) Inventors: Graham P. Lidgard, Madison, WI (US); Michael J. Domanico, Madison, WI (US); Hatim Allawi, Middleton, WI (US); Hongzhi Zou, Middleton, WI (US)

(73) Assignee: Exact Sciences Corporation, Madison, WI (US)

( * ) Notice: Subject to any disclaimer, the term of this patent is extended or adjusted under 35 U.S.C. 154(b) by 209 days.

This patent is subject to a terminal disclaimer.

(21) Appl. No.: 17/170,541

(22) Filed: Feb. 8, 2021

(65) Prior Publication Data

US 2021/0222255 A1 Jul. 22, 2021

Related U.S. Application Data

(63) Continuation of application No. 16/522,500, filed on Jul. 25, 2019, now abandoned, which is a
(Continued)

(51) Int. Cl.
*C12Q 1/68* (2018.01)
*C12Q 1/6886* (2018.01)
(Continued)

(52) U.S. Cl.
CPC ........... *C12Q 1/6886* (2013.01); *C12Q 1/686* (2013.01); *C12Q 1/6827* (2013.01); *C12Q 2600/154* (2013.01)

(58) Field of Classification Search
None
See application file for complete search history.

(56) References Cited

U.S. PATENT DOCUMENTS

| 5,541,311 A | 7/1996 | Dahlberg et al. |
| 5,614,402 A | 3/1997 | Dahlberg et al. |

(Continued)

FOREIGN PATENT DOCUMENTS

| WO | WO2001077384 | 10/2001 |
| WO | WO2006050499 | 5/2006 |
| WO | WO2009117327 | 9/2009 |

OTHER PUBLICATIONS

Fackler et al. (Quantitative Multiplex Methylation-Specific PCR Assay for the Detection of Promoter Hypermethylation in Multiple Genes in Breast Cancer, Cancer Research, 64, 4442-4452, Jul. 1, 2004).*

(Continued)

*Primary Examiner* — Aaron A Priest
(74) *Attorney, Agent, or Firm* — Bozicevic, Field & Francis LLP; Shweta Chandra

(57) ABSTRACT

A method for detecting a methylated genomic locus is provided. In certain embodiments, the method comprises: a) treating a nucleic acid sample that contains both unmethylated and methylated copies of a genomic locus with an agent that modifies cytosine to uracil to produce a treated nucleic acid; b) amplifying a product from the treated nucleic acid using a first primer and a second primer, wherein the first primer hybridizes to a site in the locus that contain methylcytosines and the amplifying preferentially amplifies the methylated copies of the genomic locus, to produce an amplified sample; and c) detecting the presence of amplified methylated copies of the genomic locus in the amplified sample using a flap assay that employs an invasive oligonucleotide having a 3' terminal G or C nucleotide that corresponds to a site of methylation in the genomic locus.

16 Claims, 7 Drawing Sheets

Specification includes a Sequence Listing.

Related U.S. Application Data continuation of application No. 14/539,841, filed on Nov. 12, 2014, now abandoned, which is a continuation of application No. 12/946,745, filed on Nov. 15, 2010, now Pat. No. 8,916,344.

(51) Int. Cl.
  *C12Q 1/686* (2018.01)
  *C12Q 1/6827* (2018.01)

(56) References Cited

U.S. PATENT DOCUMENTS

| | | |
|---|---|---|
| 5,719,028 A | 2/1998 | Dahlberg et al. |
| 5,795,763 A | 8/1998 | Dahlberg et al. |
| 5,837,450 A | 11/1998 | Dahlberg et al. |
| 5,843,654 A | 12/1998 | Heisler et al. |
| 5,843,669 A | 12/1998 | Kaiser et al. |
| 5,846,717 A | 12/1998 | Brow et al. |
| 5,874,283 A | 2/1999 | Harrington et al. |
| 5,888,780 A | 3/1999 | Dahlberg et al. |
| 5,985,557 A | 11/1999 | Prudent et al. |
| 5,994,069 A | 11/1999 | Hall et al. |
| 6,001,567 A | 12/1999 | Brow et al. |
| 6,090,543 A | 7/2000 | Prudent et al. |
| 6,090,606 A | 7/2000 | Kaiser et al. |
| 6,194,149 B1 | 2/2001 | Neri et al. |
| 6,210,880 B1 | 4/2001 | Lyamichev et al. |
| 6,214,545 B1 | 4/2001 | Dong et al. |
| 6,251,594 B1 | 6/2001 | Gonzalgo et al. |
| 6,348,314 B1 | 2/2002 | Prudent et al. |
| 6,355,437 B1 | 3/2002 | Neri et al. |
| 6,358,691 B1 | 3/2002 | Neri et al. |
| 6,372,424 B1 | 4/2002 | Brow et al. |
| 6,458,535 B1 | 10/2002 | Hall et al. |
| 6,555,357 B1 | 4/2003 | Kaiser et al. |
| 6,562,611 B1 | 5/2003 | Kaiser et al. |
| 6,635,463 B2 | 10/2003 | Ma et al. |
| 6,673,616 B1 | 1/2004 | Dahlberg et al. |
| 6,692,917 B2 | 2/2004 | Neri et al. |
| 6,706,471 B1 | 3/2004 | Brow et al. |
| 6,709,815 B1 | 3/2004 | Dong |
| 6,709,819 B2 | 3/2004 | Lyamichev et al. |
| 6,759,226 B1 | 7/2004 | Ma et al. |
| 6,780,585 B1 | 8/2004 | Dong et al. |
| 6,780,982 B2 | 8/2004 | Lyamichev et al. |
| 6,872,816 B1 | 3/2005 | Hall et al. |
| 6,875,572 B2 | 4/2005 | Prudent et al. |
| 6,913,881 B1 | 7/2005 | Aizenstein et al. |
| 6,932,943 B1 | 8/2005 | Cracauer et al. |
| 7,011,944 B2 | 3/2006 | Prudent et al. |
| 7,045,289 B2 | 5/2006 | Allawi et al. |
| 7,060,436 B2 | 6/2006 | Lyamichev et al. |
| 7,067,643 B2 | 6/2006 | Dahlberg et al. |
| 7,087,381 B2 | 8/2006 | Dahlberg et al. |
| 7,101,672 B2 | 9/2006 | Dong et al. |
| 7,122,364 B1 | 10/2006 | Lyamichev et al. |
| 7,150,982 B2 | 12/2006 | Allawi et al. |
| 7,195,871 B2 | 3/2007 | Lyamichev et al. |
| 7,256,020 B2 | 8/2007 | Lyamichev et al. |
| 7,273,696 B2 | 9/2007 | Dahlberg et al. |
| 7,297,780 B2 | 11/2007 | Skrzypczynski et al. |
| 7,306,917 B2 | 12/2007 | Prudent et al. |
| 7,312,033 B2 | 12/2007 | Accola et al. |
| 7,354,708 B2 | 4/2008 | Hall et al. |
| 7,381,530 B2 | 6/2008 | Hall et al. |
| 7,384,746 B2 | 6/2008 | Lyamichev et al. |
| 7,407,782 B2 | 8/2008 | Prudent et al. |
| 7,429,455 B2 | 9/2008 | Dong et al. |
| 7,432,048 B2 | 10/2008 | Neri et al. |
| 7,435,390 B2 | 10/2008 | Cracauer et al. |
| 7,462,451 B2 | 12/2008 | Skrzypczynski et al. |
| 7,473,773 B2 | 1/2009 | Elagin et al. |
| 7,482,118 B2 | 1/2009 | Allawi et al. |
| 7,482,127 B2 | 1/2009 | Agarwal et al. |
| 7,514,220 B2 | 4/2009 | Hall et al. |
| 7,527,928 B2 | 5/2009 | Neri et al. |
| 7,527,948 B2 | 5/2009 | Hudson et al. |
| 7,541,145 B2 | 6/2009 | Prudent et al. |
| 7,582,436 B2 | 9/2009 | Hall et al. |
| 7,588,891 B2 | 9/2009 | Prudent et al. |
| 7,601,496 B2 | 10/2009 | Dahlberg et al. |
| 7,674,924 B2 | 3/2010 | Skrzypczynski et al. |
| 7,678,542 B2 | 3/2010 | Lyamichev et al. |
| 7,691,573 B2 | 4/2010 | Dahlberg et al. |
| 7,700,750 B2 | 4/2010 | Mast et al. |
| 2002/0128465 A1 | 9/2002 | Lyamichev et al. |
| 2002/0142454 A1 | 10/2002 | Cracauer et al. |
| 2002/0156255 A1 | 10/2002 | Cracauer et al. |
| 2002/0198693 A1 | 12/2002 | Marusich et al. |
| 2003/0072689 A1 | 4/2003 | Cracauer et al. |
| 2003/0082544 A1 | 5/2003 | Fors et al. |
| 2003/0092039 A1 | 5/2003 | Olson-Munoz et al. |
| 2003/0104378 A1 | 6/2003 | Allawi et al. |
| 2003/0104470 A1 | 6/2003 | Fors et al. |
| 2003/0113236 A1 | 6/2003 | Cracauer et al. |
| 2003/0113237 A1 | 6/2003 | Cracauer et al. |
| 2003/0124526 A1 | 7/2003 | Cracauer et al. |
| 2003/0134349 A1 | 7/2003 | Ma et al. |
| 2003/0143535 A1 | 7/2003 | Lyamichev et al. |
| 2003/0165954 A1 | 9/2003 | Katagiri et al. |
| 2003/0186238 A1 | 10/2003 | Allawi et al. |
| 2003/0219784 A1 | 11/2003 | Ip et al. |
| 2004/0014067 A1 | 1/2004 | Lyamichev et al. |
| 2004/0018489 A1 | 1/2004 | Ma et al. |
| 2004/0096874 A1 | 5/2004 | Neville et al. |
| 2004/0203035 A1 | 10/2004 | Mast et al. |
| 2004/0219576 A1 | 11/2004 | Skrzypczynski et al. |
| 2004/0235024 A1 | 11/2004 | Lyamichev et al. |
| 2005/0048527 A1 | 3/2005 | Allawi et al. |
| 2005/0074788 A1 | 4/2005 | Dahlberg et al. |
| 2005/0106593 A1* | 5/2005 | Markowitz .......... C12Q 1/6886 435/6.14 |
| 2005/0106596 A1 | 5/2005 | Skrzypczynski et al. |
| 2005/0130179 A1 | 6/2005 | Lyamichev et al. |
| 2005/0158716 A1 | 7/2005 | Dahlberg et al. |
| 2005/0164177 A1 | 7/2005 | Neri et al. |
| 2005/0181435 A1 | 8/2005 | Prudent et al. |
| 2005/0186588 A1* | 8/2005 | Lyamichev .......... C12Q 1/6846 435/91.2 |
| 2005/0196750 A1 | 9/2005 | Elagin et al. |
| 2005/0260630 A1 | 11/2005 | Goodman et al. |
| 2005/0272070 A1 | 12/2005 | Ehrich et al. |
| 2005/0277138 A1 | 12/2005 | Skrzypczynski et al. |
| 2006/0147938 A1 | 7/2006 | Accola et al. |
| 2006/0147955 A1* | 7/2006 | Allawi ................. C12Q 1/6823 435/91.2 |
| 2006/0160074 A1 | 7/2006 | Dorn et al. |
| 2006/0183207 A1 | 8/2006 | Lyamichev et al. |
| 2006/0198709 A1 | 9/2006 | Marusich et al. |
| 2006/0199202 A1 | 9/2006 | Lyamichev et al. |
| 2006/0234252 A1 | 10/2006 | Andersen |
| 2006/0240452 A1 | 10/2006 | Skrzypczynski et al. |
| 2006/0246475 A1 | 11/2006 | Peterson et al. |
| 2006/0252032 A1 | 11/2006 | Aslanukov et al. |
| 2007/0049745 A1 | 3/2007 | Skrzypczynski et al. |
| 2007/0087345 A1 | 4/2007 | Olson-Munoz et al. |
| 2007/0111200 A1 | 5/2007 | Hudson et al. |
| 2007/0134249 A1 | 6/2007 | Denney et al. |
| 2007/0178445 A1 | 8/2007 | Eshleman et al. |
| 2007/0202517 A1 | 8/2007 | Agarwal et al. |
| 2007/0207455 A1 | 9/2007 | Law et al. |
| 2007/0292856 A1 | 12/2007 | Lyamichev et al. |
| 2008/0014124 A1 | 1/2008 | Skrzypczynski et al. |
| 2008/0015349 A1 | 1/2008 | Skrzypczynski et al. |
| 2008/0032305 A1 | 2/2008 | Dorn et al. |
| 2008/0071074 A1 | 3/2008 | Skrzypczynski et al. |
| 2008/0131870 A1 | 6/2008 | Allawi et al. |
| 2008/0131875 A1 | 6/2008 | Hall et al. |
| 2008/0131890 A1 | 6/2008 | Allawi et al. |
| 2008/0160524 A1* | 7/2008 | Ma ...................... C12N 9/1252 435/5 |
| 2008/0176215 A1 | 7/2008 | Hudson et al. |
| 2008/0181823 A1 | 7/2008 | Iszczyszyn et al. |
| 2008/0182254 A1 | 7/2008 | Hall et al. |

(56) References Cited

U.S. PATENT DOCUMENTS

| | | |
|---|---|---|
| 2008/0182980 A1 | 7/2008 | Skrzypczynski et al. |
| 2008/0187919 A1 | 8/2008 | King et al. |
| 2008/0187926 A1 | 8/2008 | Dahlberg et al. |
| 2008/0188375 A1 | 8/2008 | Neri et al. |
| 2008/0199936 A1 | 8/2008 | Lyamichev et al. |
| 2008/0213767 A1 | 9/2008 | Western et al. |
| 2008/0220425 A1 | 9/2008 | Ma et al. |
| 2008/0261220 A1 | 10/2008 | Cracauer et al. |
| 2008/0268455 A1 | 10/2008 | Hall et al. |
| 2008/0293046 A1 | 11/2008 | Allawi et al. |
| 2009/0029869 A1 | 1/2009 | Skrzypcznski et al. |
| 2009/0041634 A1 | 2/2009 | Cracauer et al. |
| 2009/0068664 A1 | 3/2009 | Lyamichev et al. |
| 2009/0075256 A1 | 3/2009 | Lyamichev et al. |
| 2009/0078574 A1 | 3/2009 | Lyamichev et al. |
| 2009/0111092 A1 | 4/2009 | Elagin et al. |
| 2009/0117576 A1 | 5/2009 | Dong et al. |
| 2009/0142752 A1* | 6/2009 | Hall ............... C12Q 1/6858 435/6.12 |
| 2009/0142754 A1 | 6/2009 | Allawi et al. |
| 2009/0203018 A1 | 8/2009 | Agarwal et al. |
| 2009/0215043 A1 | 8/2009 | Kwitek et al. |
| 2009/0215057 A1 | 8/2009 | Tetzner |
| 2009/0253142 A1* | 10/2009 | Allawi ............. C12Q 1/6823 435/6.1 |
| 2009/0299641 A1 | 12/2009 | Allawi et al. |
| 2009/0305283 A1 | 12/2009 | Prudent et al. |
| 2010/0152431 A1 | 6/2010 | Skrzypczynski et al. |
| 2011/0136118 A1* | 6/2011 | Kreader ............ C12Q 1/6823 435/6.12 |

OTHER PUBLICATIONS

Eads et al. (MethyLight: a high-throughput assay to measure DNA methylation, Nucleic Acids Res. Apr. 15, 2000;28(8):E32).*
Rand et al. (Conversion-specific detection of DNA methylation using real-time polymerase chain reaction (ConLight-MSP) to avoid false positives, Methods 27 (2002) 114-120).*
Tadokoro et al. (Rapid quantification of periodontitis-related bacteria using a novel modification of Invader PLUS technologies, Microbiological Research 165 (2010) 43-49, Aug. 20, 2008).*
Tadokoro et al. (Quantitation of viral load by real-time PCR-monitoring Invader reaction, Journal of Virological Methods 155 (2009) 182-186, Dec. 4, 2008).*
Oler et al. (A rapid, microplate SNP genotype assay for the leptinob allele, Journal of Lipid Research vol. 49, 2008, Feb. 13, 2008); Tsuchihashi et al. (Progress in high throughput SNP genotyping methods, The Pharmacogenomics Journal (2002) 2, 103-110).*
Hosono et al. (Multiplex PCR-Based Real-Time Invader Assay (mPCR-RETINA): A Novel SNP-Based Method for Detecting Allelic Asymmetries Within Copy Number Variation Regions, Hum Mutat. Jan. 2008;29(1):182-9).*
Tang, et al. "Detection and differentiation of wild-type and vaccine mutant varicella-zoster viruses using an Invader Plus® method", Journal of Clinical Virology, vol. 40, Issue 2, pp. 129-134, 2007.
Zou, et al. "Sensitive Quantification of Vimentin Methylation with a Novel Methylation Specific qInvader Technology", Cancer/Tumor Markers AACC Annual Meeting 2010, Abstract No. D-144, 2010, p. A199.
Aoyagi, PCR, in Molecular Biology Problem Solver: A Laboratory Guide, Ch. 11, Dec. 2001, Table 11.8, pp. 291-329.
Diehl et al., "Analysis of Mutations in DNA Isolated From Plasma and Stool of Colorectal Cancer Patients", Gastroenterology, Aug. 2008, 135(2): 489.
Bailey et al., "MS-qFRET: A quantum dot-based method for analysis of DNA methylation", Genome Research, Aug. 2009, 19(8): 1455-1461.
Zou et al., "A Novel Method to Capture Methylated Human DNA from Stool: Implications for Colorectal Cancer Screening", Clinical Chemistry, Sep. 2007, 53(9): 1646-1651.

Qureshi et al., "Utility of DNA methylation markers for diagnosing cancer", International Journal of Surgery, Feb. 6, 2010, 8(3): 194-198.
Huang et al., "Hypermethylation of SFRP2 as a Potential Marker fro Stool-Based Detection of Colorectal Cancer and Precancerous Lesions", Dig Dis Sci., Apr. 5, 2007, 52(9): 2287-2291.
Kim et al., "Promoter DNA Methylation of Oncostatin M receptor-β as a Novel Diagnostic and Therapeutic Marker in Colon Cancer", PLoS One, Aug. 2009, 4(8):e6555.
Li et al., "Sensitive digital quantification of DNA methylation in clinical samples", Nature Biotechnology, Aug. 16, 2009, 27(9): 858-863.
Zhang et al., "DNA Stool Test for Colorectal Cancer: Hypermethylation of the Secreted Frizzled-Related Protein-1 Gene", Dis Colon Rectum, Aug. 16, 2007, 50(10): 1618-1627.
Ahlquist, et al., "Next-Generation Stool DNA Test Accurately Detects Colorectal Cancer and Large Adenomas", Gastroenterology, Feb. 2012, 142:248-256.
Ahlquist, et al., "The Stool DNA Test is More Accurate Than the Plasma Septin 9 Test in Detecting Colorectal Neoplasia", Clinical Gastroenterology and Hepatology, Mar. 2012, 10:272-277.
Heigh, et al., "Detection of Colorectal Serrated Polyps by Stool DNA Testing: Comparison with Fecal Immunochemical Testing for Occult Blood (FIT)", PLoS One, Jan. 2014, 9(1):e85659.
Imperiale, et al., "Multitarget Stool DNA Testing for Colorectal-Cancer Screening", The New England Journal of Medicine, Mar. 19, 2014, 370(14):1287-1297.
Lidgard, et al., "Clinical Performance of an Automated Stool DNA Assay for Detection of Colorectal Neoplasia", Clinical Gastroenterology and Hepatology, Oct. 2013, 11(10):1313-1318.
Zhou, et al. "Sensitive quantification of vimentin methylated with a novel methylation specific qinvader technology", Cancer/Tumer Markers, Clinical Chemistry, vol. 56, No. 6, Jul. 28, 2010, 1 Page.
Zou, et al. "Sensitive quantification of methylated marker with a novel methylation specific technology", Exact Science Corporation, Jul. 28, 2010, 1 page.
Rand et al., "Conversion-specific detection of DNA methylation using real-time polymerase chain reaction (ConLight-MSP) to avoid false positives", Methods, 2002, 27: 114-120.
Allawi et al., "Invader Plus Method Detects Herpes Simplex Virus in Cerebrospinal Fluid and Simultaneously Differentiates Types 1 and 2", Journal of Clinical Microbiology, Sep. 2006, p. 3443-3447.
Tadokoro et al., Rapid quantification of periodontitis-related bacteria using a novel modification of Invader PLUS technologies, Microbiological Research, 2010, 165: 43-49.
Oler et al., "A rapid, microplate SNP genotype assay for the leptinob allele", Journal of Lipid Research, vol. 49, 2008, Feb. 13, 2008.
Tsuchihashi et al., "Progress in high throughput SNP genotyping methods", The Pharmacogenomics Journal, 2002, 2: 103-110.
Hosono et al., "Multiplex PCR-Based Real-Time Invader Assay (mPCR-RETINA): A Novel SNP-Based Method for Detecting Allelic Asymmetries Within Copy Number Variation Regions", Hum Mutat., Jan. 2008, 29(1):182-189.
Ahlquist, et al., "Next-Generation Stool DNA Test Accurately Detects Colorectal Cancer and Large Adenomas", Gastroenterology, 2012;142:248-256.
Ahlquist, et al., "The Stool DNA Test is More Accurate Than the Plasma Septin 9 Test in Detecting Colorectal Neoplasia", Clinical Gastroenterology and Hepatology, 2012;10:272-277.
Allawi, et al., "Invader plus method detects herpes simplex virus in cerebrospinal fluid and simultaneously differentiates types 1 and 2", J Clin Microbiol., 2006, 44:3443-7.
Applied Biosystems, "Methylation Analysis by Bisulfite Sequencing: Chemistry, Products and Protocols from Applied Biosystems", 2007, 52pgs.
Aoyagi, et al. "PCR, in Molecular Biology Problem Solver: A Laboratory Guide", (ed A. S. Gerstein), John Wiley & Sons, Inc., New York, USA. doi:10.1002/0471223905.ch11, 2001.
Bearzatto, et al., "p16INK4A Hypermethylation Detected by Fluorescent Methylationspecific PCR in Plasmas from Non-Small Cell Lung Cancer1", 3782 vol. 8, 3782-3787, 2002.
Coen, et al. "The Polymerase Chain Reaction", Current Protocols in Molecular Biology, 3 pages, 2006.

(56) References Cited

OTHER PUBLICATIONS

Communication issued by the European Patent Office for EP application No. 11842202.1, dated Mar. 18, 2014, 8 pages.

Eads, et al., "MethyLight: a high-throughput assay to measure DNA methylation", Nucleic Acids Res., 2000, 28:E32, 8pgs.

Fackler, et al. "Quantitative multiplex methylation-specific PCR assay for the detection of promoter hypermethylation in multiple genes in breast cancer", Cancer Res. Jul. 1, 2004;64(13):4442-52.

Heigh, et al., "Detection of Colorectal Serrated Polyps by Stool DNATesting: Comparison with Fecal Immunochemical Testing for Occult Blood (FIT)", PLoS One, 9(1):e856592014, 2014.

Herman, et al., "Methylation-specific PCR: a novel PCR assay for methylation status of CpG islands", Proc Natl Acad Sci., 1996, 93:9821-6.

Imperiale, et al., "Multitarget Stool DNA Testing for Colorectal-Cancer Screening", The New England Journal of Medicine, 370(14):1287-97, 2014.

Itzkowitz, et al., "A simplified, noninvasive stool DNA test for colorectal cancer detection", Am J Gastroenterol., 2008, 103:2862-70.

Itzkowitz, et al., "Improved fecal DNA test for colorectal cancer screening", Clin Gastroenterol Hepatol., 2007, 5:111-7.

Kristensen, et al., "Sensitive Melting Analysis after Real Time -Methylation Specific PCR (SMART-MSP): high-throughput and probe-free quantitative DNA methylation detection", Nucleic Acids Research, 2008, 1-13.

Ligand, et al., "Clinical Performance of an Automated Stool DNA Assay for Detection of Colorectal Neoplasia", Clinical Gastroenterology and Hepatology, 2013;11:1313-1318.

Lo, et al., "Quantitative Analysis of Aberrant p16 Methylation Using Real-Time Quantitative Methylation-specific Polymerase Chain Reaction 1", Cancer Res 1999;59:3899-3903.

Lorente, et al., "Detection of methylation in promoter sequences by melting curve analysis-based semiquantitative real time PCR", BMC Cancer, 2008, 8:61.

Lyamichev, et al. "Polymorphism identification and quantitative detection of genomic DNA by invasive cleavage of oligonucleotide probes", Nat Biotechnol. Mar. 1999;17(3):292-6.

Palmisano, et al., "Predicting lung cancer by detecting aberrant promoter methylation in sputum", Cancer Res., 60(21):5954-8, 2000.

PCT/US11/58997 International Search Report and Written Opinion, dated Feb. 27, 2012, 11pgs.

Qiagen, "EpiTect® MethyLight PCR Handbook", MethyLight PCR Kit, MethyLight PCR + ROX Vial Kit, 2008, 36pgs.

Rand, et al. "Conversion-specific detection of DNA methylation using real-time polymerase chain reaction (ConLight-MSP) to avoid false positives", Methods. Jun. 2002;27(2):114-20.

Ruano, et al. "Biphasic amplification of very dilute DNA samples via 'booster' PCR", Nucleic Acids Res. Jul. 11, 1989; 17(13): 5407.

Tadokoro, et al., "Quantitation of viral load by real-time PCR-monitoring Invader reaction", J Virol Methods., 2009, 155:182-6.

Weisenberger, et al., "DNA methylation analysis by digital bisulfite genomic sequencing and digital MethyLight", Nucleic Acids Research, 2008, vol. 36, No. 14 4689-4698.

White, et al. "Polymerase Chain Reaction (PCR): Design and Optimization of Reactions", Encyclopedia of Life Sciences, 2005.

Yamada, et al., "Fluorometric identification of 5-methylcytosine modification in DNA: combination of photosensitized oxidation and invasive cleavage", Bioconjug Chem., 2008, 19:20-3.

Zymo Research Corp., "EZ DNA Methylation-Gold™ Kit", Flyer, Catalog Nos. D5005 & D5006, Ver. 2.1.0, downloaded Feb. 23, 2011, 2pgs.

Zymo Research Corp., "EZ DNA Methylation-Gold™ Kit", Instructions, Catalog Nos. D5005 & D5006, Ver. 2.1.0, downloaded Feb. 23, 2011, 10pgs.

Zymo Research Corp., "EZ DNA Methylation™ Kit", Instruction Manual, Catalog Nos. D5001 & D5002, Ver. 1.2.2, downloaded Feb. 23, 2011, 10pgs.

Zymo Research Corp., "Material Safety Data Sheet", MSDS: CT Conversion Reagent, Creation Date: Apr. 28, 2003, Revision Date: May 4, 2009, 1-4.

\* cited by examiner

Human vimentin sequence (VIM) fragment showing methylation and bisulfite conversion of unmethylated sequences

Unmethylated sequence (SEQ ID NO:16)

CCGTGTCCTCGTCCTCCTACCGCAGGATGTTCGGCGGCCCGGCACCGCG
AGCCGGCCAGCCGGGAGCGGAGTTCAGCCGGGAGCTAGTCACCGCACCTA

Methylated sequence (underlined methylcytosines) SEQ ID NO:17

CCGTGTCCTCGTCCTCCTACCGCAGGATGTTCGGCGGCCCGGCACCGCG
AGCCGGCCAGCCGGGAGCGGAGTTCAGCCGGGAGCTAGTCACCGCACCTA

Bisulfite Treatment

Unmethylated Sequence, after bisulfite reaction (unmethylated C becomes deoxyU) SEQ ID NO:18

UUGUGUUUGUUUGUGUUUGUUUUAUGUAGGAUGUUUGGUGGUUUGGGUAUUGUG
AGUUGGUUGAGUUAGUUUAGUUGAGUUAGUUUAUUUGUAUUUA

Methylated Sequence, after bisulfite reaction (unmethylated C becomes deoxyU) SEQ ID NO:19

UCGUGUUUCGUUUCGUUUUAUCGUAGGAUGUUCGGCGGUUCGGGUAUCGG
AGUCGGUCGAGUUCGAGUUCGAGUUAGUUUAUUUGUAUUUA

FIG. 3

Alignment of primers and flap probe, after bisulfite conversion of cytosines:

```
VIM unmethylated                1  UUGTGTUUTUGTUUTUUTAUUGUAGGAUGUUGGUGGUUUGGGUAUUGUG  50
(mismatches w/primers                              x         x        x x
or probes)
VIM methylated                  1  UCGTGUUUCGUUUUAUCGUAGGAUGUUCGGGUUCGGGUAUCGCG      50

Forward Primer                                                     GGCGGTTCGGGTATCG
Flap Probe                                                         gacgcggag-GCG
(First 9 bases are the flap)

VIM unmethylated               51  AGUUGGUUGAGUUUUAGUUGGAGUUAUGUGAUUAUGUUUAUUUGUAUUTA  100
(mismatches w/primers                       x x              x       x
or probes)
VIM methylated                 51  AGUCGGUCGAGUUUUAGUCGGAGUUACGUGAUUACGUUUAUUCGUAUUTA 100

Flap Probe (continued)             AGTCGGTCG/3C6/
Reverse Primer                                  3'-TCAGCCTCAATGCACTAATGC-5'
```

FIG. 4

METHYLATION ASSAY

CROSS-REFERENCE TO RELATED APPLICATIONS

This application is a continuation of U.S. patent application Ser. No. 16/522,500, filed on Jul. 25, 2019, which is a continuation of U.S. patent application Ser. No. 14/539,841, filed on Nov. 12, 2014, which is a continuation of U.S. patent application Ser. No. 12/946,745, filed on Nov. 15, 2010, now issued as U.S. Pat. No. 8,916,344, which applications are incorporated by reference herein.

BACKGROUND

The methylation of cytosine residues in DNA is an important epigenetic alteration in eukaryotes. In humans and other mammals methylcytosine is found almost exclusively in cytosine-guanine (CpG) dinucleotides. DNA methylation plays an important role in gene regulation and changes in methylation patterns are involved in human cancers and certain human diseases. Among the earliest and most common genetic alterations observed in human malignancies is the aberrant methylation of CpG islands, particularly CpG islands located within the 5' regulatory regions of genes, causing alterations in the expression of such genes. Consequently, there is great interest in using DNA methylation markers as diagnostic indicators for early detection, risk assessment, therapeutic evaluation, recurrence monitoring, and the like. There is also great scientific interest in DNA methylation for studying embryogenesis, cellular differentiation, transgene expression, transcriptional regulation, and maintenance methylation, among other things.

This disclosure relates to the detection of methylated DNA in a sample.

SUMMARY

A method for detecting a methylated genomic locus is provided. In certain embodiments, the method comprises: a) treating a nucleic acid sample that contains both unmethylated and methylated copies of a genomic locus with an agent that modifies cytosine to uracil to produce a treated nucleic acid; b) amplifying a product from the treated nucleic acid using a first primer and a second primer, wherein the first primer hybridizes to a site in the locus that contain methylcytosines and the amplifying preferentially amplifies the methylated copies of the genomic locus, to produce an amplified sample; and c) detecting the presence of amplified methylated copies of the genomic locus in the amplified sample using a flap assay that employs an invasive oligonucleotide having a 3' terminal G or C nucleotide that corresponds to a site of methylation in the genomic locus.

BRIEF DESCRIPTION OF THE FIGURES

FIG. 3 show the nucleotide sequences of methylated and unmethylated copies of a fragment of the human vimentin gene (VIM), before and after bisulfite treatment.

FIG. 4 shows the nucleotide sequences of an exemplary forward primer, an exemplary reverse primer, and an exemplary flap oligonucleotide, aligned with the fragments shown in FIG. 3. The nucleotide sequences shown in FIG. 4 are set forth in the sequence listing as VIM unmethylated (SEQ ID NO:18), VIM methylated (SEQ ID NO:19), SEQ ID NO:13 (forward primer), SEQ ID NO:15 (flap probe), and SEQ ID NO: 14 (reverse primer).

DEFINITIONS

Figure 1:
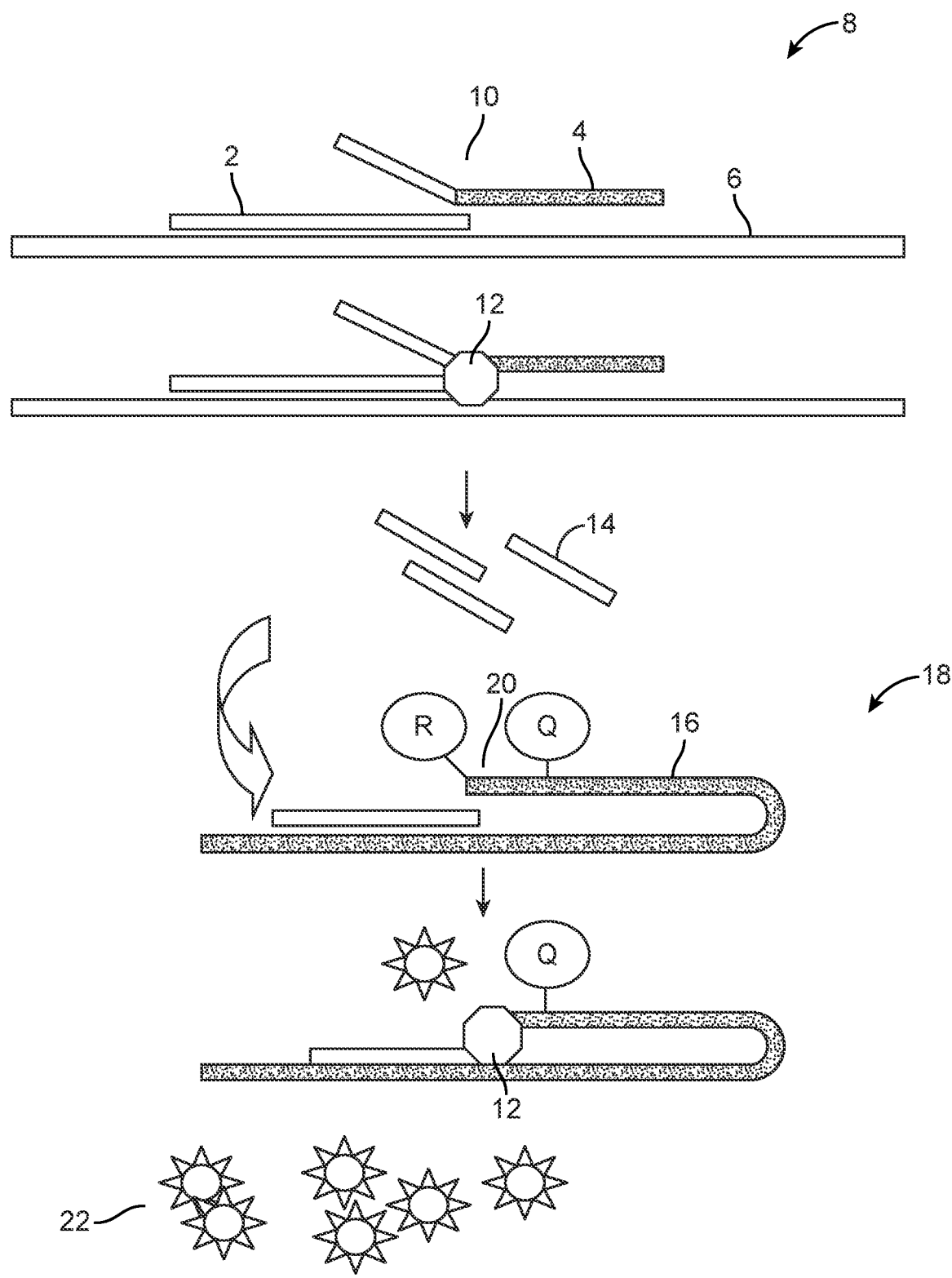
FIG. 1 schematically illustrates some of the general principles of a flap assay.

The term "sample" as used herein relates to a material or mixture of materials, typically, although not necessarily, in liquid form, containing one or more analytes of interest.

The term "nucleotide" is intended to include those moieties that contain not only the known purine and pyrimidine bases, but also other heterocyclic bases that have been modified. Such modifications include methylated purines or pyrimidines, acylated purines or pyrimidines, alkylated riboses or other heterocycles. In addition, the term "nucleotide" includes those moieties that contain hapten or fluorescent labels and may contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, are functionalized as ethers, amines, or the like.

The term "nucleic acid" and "polynucleotide" are used interchangeably herein to describe a polymer of any length, e.g., greater than about 2 bases, greater than about 10 bases, greater than about 100 bases, greater than about 500 bases, greater than about 1000 bases, up to about 10,000 or more bases composed of nucleotides, e.g., deoxyribonucleotides or ribonucleotides, and may be produced enzymatically or synthetically (e.g., PNA as described in U.S. Pat. No. 5,948,902 and the references cited therein) which can hybridize with naturally occurring nucleic acids in a sequence specific manner analogous to that of two naturally occurring nucleic acids, e.g., can participate in Watson-Crick base pairing interactions. Naturally-occurring nucleotides include guanine, cytosine, adenine and thymine (G, C, A and T, respectively).

The term "nucleic acid sample," as used herein denotes a sample containing nucleic acid.

The term "target polynucleotide," as used herein, refers to a polynucleotide of interest under study. In certain embodiments, a target polynucleotide contains one or more target sites that are of interest under study.

The term "oligonucleotide" as used herein denotes a single stranded multimer of nucleotides of about 2 to 200 nucleotides. Oligonucleotides may be synthetic or may be made enzymatically, and, in some embodiments, are 10 to 50 nucleotides in length. Oligonucleotides may contain ribonucleotide monomers (i.e., may be oligoribonucleotides) or deoxyribonucleotide monomers. An oligonucleotide may be 10 to 20, 11 to 30, 31 to 40, 41 to 50, 51 to 60, 61 to 70, 71 to 80, 80 to 100, 100 to 150 or 150 to 200 nucleotides in length, for example.

The term "duplex," or "duplexed," as used herein, describes two complementary polynucleotides that are base-paired, i.e., hybridized together.

The term "primer" as used herein refers to an oligonucleotide that has a nucleotide sequence that is complementary to a region of a target polynucleotide. A primer binds to the complementary region and is extended, using the target nucleic acid as the template, under primer extension conditions. A primer may be in the range of about 15 to about 50 nucleotides although primers outside of this length may be used. A primer can be extended from its 3' end by the action of a polymerase. An oligonucleotide that cannot be extended from its 3' end by the action of a polymerase is not a primer.

The term "extending" as used herein refers to any addition of one or more nucleotides to the 3' end of a nucleic acid, e.g. by ligation of an oligonucleotide or by using a polymerase.

The term "amplifying" as used herein refers to generating one or more copies of a target nucleic acid, using the target nucleic acid as a template.

The term "denaturing," as used herein, refers to the separation of a nucleic acid duplex into two single strands.

The terms "determining", "measuring", "evaluating", "assessing," "assaying," 'detecting," and "analyzing" are used interchangeably herein to refer to any form of measurement, and include determining if an element is present or not. These terms include both quantitative and/or qualitative determinations. Assessing may be relative or absolute. "Assessing the presence of" includes determining the amount of something present, as well as determining whether it is present or absent.

The term "using" has its conventional meaning, and, as such, means employing, e.g., putting into service, a method or composition to attain an end.

As used herein, the term "$T_m$" refers to the melting temperature of an oligonucleotide duplex at which half of the duplexes remain hybridized and half of the duplexes dissociate into single strands. The $T_m$ of an oligonucleotide duplex may be experimentally determined or predicted using the following formula $T_m=81.5+16.6(\log_{10}[Na^+])+0.41$ (fraction G+C)−(60/N), where N is the chain length and [$Na^+$] is less than 1 M. See Sambrook and Russell (2001; Molecular Cloning: A Laboratory Manual, $3^{rd}$ ed., Cold Spring Harbor Press, Cold Spring Harbor N.Y., ch. 10). Other formulas for predicting $T_m$ of oligonucleotide duplexes exist and one formula may be more or less appropriate for a given condition or set of conditions.

As used herein, the term "$T_m$-matched" refers to a plurality of nucleic acid duplexes having $T_m$s that are within a defined range, e.g., within 5° C. or 10° C. of each other.

As used herein, the term "reaction mixture" refers to a mixture of reagents that are capable of reacting together to produce a product in appropriate external conditions over a period of time. A reaction mixture may contain PCR reagents and flap cleavage reagents, for example, the recipes for which are independently known in the art.

The term "mixture", as used herein, refers to a combination of elements, that are interspersed and not in any particular order. A mixture is heterogeneous and not spatially separable into its different constituents. Examples of mixtures of elements include a number of different elements that are dissolved in the same aqueous solution, or a number of different elements attached to a solid support at random or in no particular order in which the different elements are not spatially distinct. A mixture is not addressable. To illustrate by example, an array of spatially separated surface-bound polynucleotides, as is commonly known in the art, is not a mixture of surface-bound polynucleotides because the species of surface-bound polynucleotides are spatially distinct and the array is addressable.

As used herein, the term "PCR reagents" refers to all reagents that are required for performing a polymerase chain reaction (PCR) on a template. As is known in the art, PCR reagents essentially include a first primer, a second primer, a thermostable polymerase, and nucleotides. Depending on the polymerase used, ions (e.g., $Mg^{2+}$) may also be present. PCR reagents may optionally contain a template from which a target sequence can be amplified.

As used herein, the term "flap assay" refers to an assay in which a flap oligonucleotide is cleaved in an overlap-dependent manner by a flap endonuclease to release a flap that is then detected. The principles of flap assays are well known and described in, e.g., Lyamichev et al. (Nat. Biotechnol. 1999 17:292-296), Ryan et al (Mol. Diagn. 1999 4:135-44) and Allawi et al (J Clin Microbiol. 2006 44: 3443-3447). For the sake of clarity, certain reagents that are employed in a flap assay are described below. The principles of a flap assay are illustrated in FIG. 1. In the flap assay shown in FIG. 1, an invasive oligonucleotide 2 and flap oligonucleotide 4 are hybridized to target 6 to produce a first complex 8 that contains a nucleotide overlap at position 10. First complex 8 is a substrate for flap endonuclease. Flap endonuclease 12 cleaves flap oligonucleotide 4 to release a flap 14 that hybridizes with FRET cassette 16 that contains a quencher "Q" and a nearby quenched flourophore "R" that is quenched by the quencher Q. Hybridization of flap 14 to FRET cassette 16 results in a second complex 18 that contains a nucleotide overlap at position 20. The second complex is also a substrate for flap endonuclease. Cleavage of FRET cassette 16 by flap endonuclease 12 results in release of the fluorophore 22, which produces a fluorescent signal. These components are described in greater detail below.

As used herein, the term "invasive oligonucleotide" refers to an oligonucleotide that is complementary to a region in a target nucleic acid. The 3' terminal nucleotide of the invasive oligonucleotide may or may not base pair a nucleotide in the target (e.g., which may be 5-methylcytosine or uracil, for example).

As used herein, the term "flap oligonucleotide" refers to an oligonucleotide that contains a flap region and a region that is complementary to a region in the target nucleic acid. The target complementary regions on the invasive oligonucleotide and the flap oligonucleotide overlap by a single nucleotide such that, when they are annealed to the target nucleic acid, the complementary sequences overlap. As is known, if: a) the 3' terminal nucleotide of the invasive nucleotide and b) the nucleotide that overlaps with that nucleotide in the flap oligonucleotide both base pair with a nucleotide in the target nucleic acid, then a particular structure is formed. This structure is a substrate for an enzyme, defined below as a flap endonuclease, that cleaves the flap from the target complementary region of the flap oligonucleotide. If the 3' terminal nucleotide of the invasive oligonucleotide does not base pair with a nucleotide in the target nucleic acid, or if the overlap nucleotide in the flap oligononucleotide does not base pair with a nucleotide in the target nucleic acid, the complex is not a substrate for the enzyme.

The term "flap endonuclease" or "FEN" for short, as used herein, refers to a class of nucleolytic enzymes that act as structure specific endonucleases on DNA structures with a duplex containing a single stranded 5' overhang, or flap, on one of the strands that is displaced by another strand of nucleic acid, i.e., such that there are overlapping nucleotides at the junction between the single and double-stranded DNA. FENs catalyze hydrolytic cleavage of the phosphodiester bond at the junction of single and double stranded DNA, releasing the overhang, or the flap. Flap endonucleases are reviewed by Ceska and Savers (Trends Biochem. Sci. 1998 23:331-336) and Liu et al (*Annu. Rev. Biochem.* 2004 73: 589-615). FENs may be individual enzymes, multi-subunit enzymes, or may exist as an activity of another enzyme or protein complex, e.g., a DNA polymerase. A flap endonuclease may be thermostable.

As used herein, the term "cleaved flap" refers to a single-stranded oligonucleotide that is a cleavage product of a flap assay.

As used herein, the term "FRET cassette" refers to a hairpin oligonucleotide that contains a fluorophore moiety and a nearby quencher moiety that quenches the fluorophore. Hybridization of a cleaved flap with a FRET cassette produces a secondary substrate for the flap endonuclease. Once this substrate is formed, the 5' fluorophore-containing base is cleaved from the cassette, thereby generating a fluorescence signal.

As used herein, the term "flap assay reagents" refers to all reagents that are required for performing a flap assay on a substrate. As is known in the art, flap assays include an invasive oligonucleotide, a flap oligonucleotide, a flap endonuclease and a FRET cassette, as described above. Flap assay reagents may optionally contain a target to which the invasive oligonucleotide and flap oligonucleotide bind.

As used herein, the term "genomic locus" refers to a defined region in a genome. A genomic locus exists at the same location in the genomes of different cells from the same individual, or in different individuals. A genomic locus in one cell or individual has a nucleotide sequence that is identical or very similar (i.e., more than 99% identical) to the same genomic locus in a different cell or individual. The difference in nucleotide sequence between the same locus in different cells or individuals may be due to one or more nucleotide substitutions. A genomic locus may be defined by genomic coordinates, by name, or using a symbol. A genomic locus in a nucleic acid sample that has been treated with an agent that modifies unmethylated cytosine to uracil has the same sequence as the genomic locus in an unmethylated sample, except that unmethylated cytosines in the sequence (but not methylated cytosines) are modified to be become uracils. In amplified copies of a genomic locus in a nucleic acid sample that has been treated with such an agent, the uracil is converted to thymine.

As used herein, the term "methylation state" refers to the presence or absence of a methyl group on a cytosine residue at a site of methylation. For clarity, a cytosine that is unmethylated will be referred to as "unmethylated cytosine" or "unmethylated C", and a cytosine that is methylated (i.e., 5-methylcytosine) will be referred to as "methylated cytosine," "methylated C," or "methyl C."

As used herein, a "site of methylation" refers to the position of a cytosine nucleotide that is known to be at least sometimes methylated in a genomic locus. The cytosine at a site of methylation can be an unmethylated cytosine or a methylated cytosine. In other words, the term "site of methylation" refers to a specific cytosine in a genomic locus, the methylation state of which is sought to be determined. The site of methylation may be defined by genomic coordinates, or coordinates relative to the start codon of a gene, for example.

As will be described in greater detail below, certain embodiments of the subject method involve treating a nucleic acid sample with an agent that specifically converts unmethylated cytosine to uracil by deamination. Therefore, in an untreated sample, the site of methylation will occupied by an unmethylated cytosine or a methylated cytosine, depending on the methylation status of that site. Likewise, the site of methylation in a treated sample will be occupied by a methylated cytosine or a uracil, depending on the methylation status of that site in the sample prior to treatment.

The term "corresponds to" and grammatical equivalents, e.g., "corresponding", as used herein refers to a specific relationship between the elements to which the term refers. For example, an oligonucleotide that corresponds to a sequence in a longer nucleic acid contains the same nucleotide sequence as or is complementary to a nucleotide sequence in the nucleic acid.

In the context of a nucleotide in an oligonucleotide that corresponds to a site of methylation or a nucleotide in an oligonucleotide that corresponds to a methylated cytosine, the term "corresponds to" and grammatical equivalents thereof are intended to identify the nucleotide that is correspondingly positioned relative to (i.e., positioned across from) a site of methylation when the two nucleic acids (e.g., an oligonucleotide and genomic DNA containing a methylated cytosine) are aligned or base paired. Again, unless otherwise indicated (e.g., in the case of a nucleotide that "does not base pair" or "base pairs" with a particular residue) a nucleotide that "corresponds to" a site of methylation base pairs with either a methylated site or an unmethylated site. For clarity, in an oligonucleotide, a G or C nucleotide at a position that corresponds to a methylated cytosine in a sequence, e.g., a genomic locus, can: a) base pair with a methylated cytosine in the sequence, b) base pair a cytosine that positionally corresponds to the methylated cytosine in an amplified version of the sequence, or c) base pair with a G residue that is complementary to such a cytosine in an amplified sequence.

As will be described in greater detail below, the subject method may also involve amplifying a nucleic acid product sample that has been treated with an agent that specifically converts unmethylated cytosine to uracil (see, for example, Frommer et a. Proc. Natl. Acad. Sci. 1992 89:1827-1831). As a result of the amplification step, methylated cytosines are converted to cytosines, and uracils are converted to thymines. The methylation state of a cytosine nucleotide in the initial sample can therefore be evaluated by determining whether a base-pair in the amplification product that is at the same position as the cytosine in question is a C/G base pair (which indicates that the cytosine in question is methylated) or an A/T base pair (which indicates that the cytosine residue is unmethylated). Thus, the methylation status of a cytosine in an initial sample can be determined by amplifying a double stranded product from a sample that has been treated with an agent that specifically converts unmethylated cytosine to uracil, and then examining the position corresponding to the target cytosine in either of the strands (i.e., either the top strand or the bottom strand) of the amplification product to determine whether an A or T is present (which indicates that the cytosine in question is methylated), or if a G or C is present (which indicates that the cytosine in question is methylated). Thus, in the context of an oligonucleotide that hybridizes to a double stranded amplification product produced by amplification of a genomic locus from a sample that has been treated with an agent that specifically converts unmethylated cytosine to uracil, a nucleotide that "corresponds to" a site of methylation is a nucleotide that base pairs with either the top strand or the bottom strand at the site of methylation.

As used herein, a "sequence that is methylated" is a nucleotide sequence that contains a site of methylation, i.e., a cytosine nucleotide that is known to be at least sometimes methylated.

As used herein, the term "unmethylated", with reference a nucleotide sequence, refers to the copies of a sequence that are not methylated.

As used herein, the term "methylated", with reference a nucleotide sequence, refers to copies of a sequence that contain 5-methylcytosine. Methylation of a genomic locus may, e.g., alter the expression of a protein, which causes a phenotypic change (e.g., a cancer-related phenotype) in the cells that have such a methylated locus. Alternatively, methylation of a genomic locus may be silent.

A sample that comprises "both unmethylated and methylated copies of a genomic locus" and grammatical equivalents thereof, refers to a sample that contains multiple DNA molecules of the same genomic locus, where the sample contains both unmethylated copies of the genomic locus and methylated copies of the same locus. In this context, the term "copies" is not intended to mean that the sequences were copied from one another. Rather, the term "copies" in intended to indicate that the sequences are of the same locus in different cells or individuals. In other words, a sample contains a mixture of nucleic acid molecules having the same nucleotide sequence, except that some of the molecules contain methylated cytosine residues.

As used herein, the term "degree of methylation" refers to the relative number, percentage, or fraction of members of a particular target nucleotide species within a sample that are methylated compared to those members of that particular target nucleotide species that are not methylated.

As used herein, the term "an agent that modifies unmethylated cytosine to uracil" refers to any agent that specifically deaminates unmethylated cytosine to produce uracil. Such agents are specific in that they do not deaminate 5-methylcytosine to produce uracil. Bisulfite is an example of such an agent.

As used herein, the term "a treated nucleic acid sample" is a nucleic acid sample that has been treated with an agent that modifies unmethylated cytosine to uracil.

As used herein, the term "initial sample" refers to a sample that has not been treated with an agent that modifies unmethylated cytosine to uracil.

As used herein the term "nucleotide sequence" refers to a contiguous sequence of nucleotides in a nucleic acid. As would be readily apparent, the number of nucleotides in a nucleotide sequence may vary greatly. In particular embodiments, a nucleotide sequence (e.g., of an oligonucleotide) may be of a length that is sufficient for hybridization to a complementary nucleotide sequence in another nucleic acid. In these embodiments, a nucleotide sequence may be in the range of at least 10 to 50 nucleotides, e.g., 12 to 20 nucleotides in length, although lengths outside of these ranges may be employed in many circumstances.

As used herein the term "fully complementary to" in the context of a first nucleic acid that is fully complementary to a second nucleic acid refers to a case when every nucleotide of a contiguous sequence of nucleotides in a first nucleic acid base pairs with a complementary nucleotide in a second nucleic acid.

As used herein the term a "primer pair" is used to refer to two primers that can be employed in a polymerase chain reaction to amplify a genomic locus. A primer pair may in certain circumstances be referred to as containing "a first primer" and "a second primer" or "a forward primer" and "a reverse primer". Use of any of these terms is arbitrary and is not intended to indicate whether a primer hybridizes to a top strand or bottom strand of a double stranded nucleic acid.

A "CpG" island is defined as a region of DNA of greater than 500 bp with a G/C content of at least 55% and an observed CpG/expected CpG ratio of at least 0.65, as defined by Takai et al Proc. Natl. Acad. Sci. 2002 99: 3740-3745). Use of this formula to identify CpG islands excludes other GC-rich genomic sequences such as Alu repeats.

DESCRIPTION OF EXEMPLARY EMBODIMENTS

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It must be noted that as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

In the following description, the skilled artisan will understand that any of a number of polymerases and flap endonucleases could be used in the methods, including without limitation, those isolated from thermostable or hyperthermostable prokaryotic, eukaryotic, or archaeal organisms. The skilled artisan will also understand that the enzymes that are used in the method, e.g., polymerase and flap endonuclease, include not only naturally occurring enzymes, but also recombinant enzymes that include enzymatically active fragments, cleavage products, mutants, and variants of wild type enzymes.

In further describing the method, the reagent mixture used in the method will be described first, followed by a description of the method by which a sample may be treated and the reaction conditions that may be used in the method.

Reaction Mixture

The reaction mixture may vary depending how the reaction is performed, e.g., whether, for example, one or both of the first and second primers hybridize to methylated sequences, or whether the first primer (which is used for amplification of a genomic locus) is also employed as an invasive oligonucleotide in the flap assay, in which case no distinct invasive oligonucleotide need be included in the assay mixture.

In general terms, the reaction mixture used in the method may generally contain: a) amplification reagents comprising a thermostable polymerase, nucleotides, a first primer and a second primer for amplifying a target genomic locus from a treated nucleic acid sample; wherein: i. the first primer hybridizes to a methylated sequence in the genomic locus and optionally contains a 3' G or C terminal nucleotide that corresponds to a methylated cytosine in the genomic locus; and ii. the reagents preferentially amplify methylated copies of the genomic locus, to produce an amplified sample; b) flap assay reagents comprising a flap endonuclease, a FRET cassette, a flap oligonucleotide and, if the first primer does not contain a 3' terminal nucleotide that corresponds to the methylated cytosine, an invasive oligonucleotide, that is distinct from the first primer, that has a 3' terminal G or C nucleotide that corresponds to the methylated cytosine; and c) the treated nucleic acid sample, wherein the treated nucleic acid sample is made by treating an initial nucleic acid sample comprising both methylated copies and unmethylated copies of the genomic locus with an agent that modifies unmethylated cytosine to uracil. The flap oligonucleotide contains a G or C nucleotide at a position that corresponds to the methylated cytosine. The reaction mixture is characterized in that it can amplify and detect the presence of methylated copies of the genomic locus in the sample.

As noted above, the amplification generally employs a first primer that hybridizes to a methylated sequence in a genomic locus and preferentially amplifies methylated copies of the genomic locus. In certain embodiments, the first primer may contain one or more nucleotides (e.g., G residues) that base pair with corresponding methylated cytosine nucleotides in the methylated sequence (which would have been converted to a uracil if they were unmethylated). In particular embodiments, the first primer may contain up to 3 or 4 nucleotides that base pair with corresponding methylated cytosines in a methylated sequence, particularly toward the 3' end of the primer thereby making the primer a methylation specific primer in that it preferentially amplifies methylated copies of the genomic locus. In one embodiment, the primer may contain a 3' terminal nucleotide that base pairs with a methylated cytosine in the methylated sequence, or base pairs with a G residue in an amplicon complementary to a methylated cytosine, as well as 1, 2 or 3 further nucleotides that base pair with other methylated cytosines or their complements in the sequence. Thus, the first primer may contain one or more internal G or C nucleotides at positions that correspond to a corresponding number of second methylated cytosine in the genomic locus.

While thereby preferential amplification of methylated copies of a genomic locus may be done using a pair of primers in which only one of the primers is methylation specific, in particular embodiments, both the first and second primers may be methylation-specific in that they both hybridize to methylated sequences in the genomic locus.

The design of the methylation-specific primers that may be present in the reaction mixture may be adapted from, e.g., the primer design methods described by, e.g., Herman et al (Methylation-specific PCR: a novel PCR assay for methylation status of CpG islands. Proc. Natl. Acad. Sci. 1996 93: 9821-6) and Ehrich et al (Quantitative high-throughput analysis of DNA methylation patterns by base-specific cleavage and mass spectrometry. Proc. Natl. Acad. Sci. 2005 102: 15785-90), as well as those reviewed in Li (Designing PCR primer for DNA methylation mapping. Methods Mol Biol. 2007 402: 371-84), Derks et al (Methylation-specific PCR unraveled. Cell Oncol. 2004 26:291-9) and Cottrell et al (Sensitive detection of DNA methylation. Ann N Y Acad. Sci. 2003 983:120-30). Since the identities of many if not most CpG islands in the human and other genomes are known, (see, e.g., Lauss et al Br. J. Cancer. MethCancerDB-aberrant DNA methylation in human cancer 2008 98: 816-817; Wang et al Bioinformatics, An evaluation of new criteria for CpG islands in the human genome as gene markers 2003 20: 1170-1177) the design of methylation-specific primers for analysis of a number of different genomic loci may be done without undue effort.

As noted above, the presence of distinct invasive oligonucleotides in the reaction mixture may depend on whether the first primer is also employed as an invasive oligonucleotide in the flap assay. As such, in some embodiments, the first primer contains a 3' terminal nucleotide that base pairs with a methylated cytosine in the sequence to which the primer binds. In these embodiments, the first primer may be employed as an invasive oligonucleotide in the flap assay and, as such, the reaction mixture need not contain an invasive oligonucleotide in addition to the first primer. In other embodiments, the first primer does not contain a 3' terminal nucleotide that base pairs with a methylated cytosine in the methylated sequence. In these embodiments, the reaction mixture may contain a distinct invasive oligonucleotide that contains a 3' terminal G or C nucleotide that corresponds to the site of methylation. In these embodiments, the 3' terminal nucleotide of the invasive oligonucleotide may base pair with a site of methylation that is internal to the sequences of the primers in the amplification product.

In alternative embodiments, the reaction mixture may comprise a first primer that contains a 3' terminal nucleotide that base pairs with a methylated cytosine or its complement in the genomic locus as well as an invasive oligonucleotide that contains a 3' terminal G or C nucleotide that corresponds to the site of methylation. In these embodiments, the 3' terminal nucleotide of the first primer and the 3' terminal nucleotide of the invasive oligonucleotide base pair with nucleotides at different sites of methylation in the genomic locus. In one embodiment, the 3' terminal nucleotide of the invasive oligonucleotide base pairs with a site of methylation that is internal to the sequences of the primers in the amplification product.

In particular embodiments, a separate invasive oligonucleotide may contain other nucleotides (e.g., G or C nucleotides) in addition to the 3' terminal nucleotide that base pair with nucleotides at other sites of methylation. In other words, a separate invasive oligonucleotides may contain one or more (e.g., 1, 2, 3 or 4 or more) internal G or C nucleotides that correspond to methylated cytosines. These internal nucleotides increase the specificity of binding of the invasive oligonucleotide to nucleic acid that has been amplified from methylated copies of the genomic locus, thereby increasing the fidelity of detection. In a similar manner, the portion of the flap oligonucleotide that hybridizes to the amplification product may contain one or more (e.g., 1, 2, 3 or 4 or more) internal G or C nucleotides that correspond to methylated cytosines, which serve to increase the specificity of binding of the flap oligonucleotide to nucleic acid that has been amplified from methylated copies of the genomic locus, thereby increasing the fidelity of detection. Thus, in some embodiments, the flap oligonucleotide may contain one or more internal G or C nucleotide positions that corresponds to a corresponding number of second methylated cytosines in the genomic locus.

The exact identities and concentrations of the reagents present in the reaction mixture may be similar to or the same as those independently employed in PCR and flap cleavage assays, with the exception that the reaction mixture contains $Mg^{2+}$ at a concentration that is higher than employed in conventional PCR reaction mixtures (which contain $Mg^{2+}$ at a concentration of between about 1.8 mM and 3 mM). In certain embodiments, the reaction mixture described herein contains $Mg^{2+}$ at a concentration of 4 mM to 10 mM, e.g., 6 mM to 9 mM. Exemplary reaction buffers and DNA polymerases that may be employed in the subject reaction mixture include those described in various publications (e.g., Ausubel, et al., Short Protocols in Molecular Biology, 3rd ed., Wiley & Sons 1995 and Sambrook et al., Molecular Cloning: A Laboratory Manual, Third Edition, 2001 Cold Spring Harbor, N.Y.). Reaction buffers and DNA polymerases suitable for PCR may be purchased from a variety of suppliers, e.g., Invitrogen (Carlsbad, Calif.), Qiagen (Valencia, Calif.) and Stratagene (La Jolla, Calif.). Exemplary polymerases include Taq, Pfu, Pwo, UlTma and Vent, although many other polymerases may be employed in certain embodiments. Guidance for the reaction components suitable for use with a polymerase as well as suitable conditions for their use is found in the literature supplied with the polymerase. Primer design is described in a variety of publications, e.g., Diffenbach and Dveksler (PCR Primer, A Laboratory Manual, Cold Spring Harbor Press 1995); R. Rapley, (The Nucleic Acid Protocols Handbook (2000), Humana Press, Totowa, N.J.); Schena and Kwok et al., Nucl. Acid Res. 1990 18:999-1005). Primer and probe design software programs are also commercially available, including without limitation, Primer Detective (ClonTech, Palo Alto, Calif.), Lasergene, (DNASTAR, Inc., Madison, Wis.), Oligo software (National Biosciences, Inc., Plymouth, Minn.), and iOligo (Caesar Software, Portsmouth, N.H).

Exemplary flap cleavage assay reagents are found in Lyamichev et al. (Nat. Biotechnol. 1999 17:292-296), Ryan et al (Mol. Diagn. 1999 4:135-44) and Allawi et al (J Clin Microbiol. 2006 44: 3443-3447). Appropriate conditions for flap endonuclease reactions are either known or can be readily determined using methods known in the art (see, e.g., Kaiser et al., J. Biol. Chem. 274:21387-94, 1999). Exemplary flap endonucleases that may be used in the method include, without limitation, *Thermus aquaticus* DNA polymerase I, *Thermus thermophilus* DNA polymerase I, mammalian FEN-1, *Archaeoglobus fulgidus* FEN-1, *Methanococcus jannaschii* FEN-1, *Pyrococcus furiosus* FEN-1, *Methanobacterium thermoautotrophicum* FEN-1, *Thermus thermophilus* FEN-1, CLEAVASE™ (Third Wave, Inc., Madison, Wis.), *S. cerevisiae* RTH1, *S. cerevisiae* RAD27, *Schizosaccharomyces pombe* rad2, bacteriophage T5 5'-3' exonuclease, *Pyroccus horikoshii* FEN-1, human exonuclease 1, calf thymus 5'-3' exonuclease, including homologs thereof in eubacteria, eukaryotes, and archaea, such as members of the class II family of structure-specific enzymes, as well as enzymatically active mutants or variants thereof. Descriptions of cleaving enzymes can be found in, among other places, Lyamichev et al., Science 260:778-83, 1993; Eis et al., Nat. Biotechnol. 19:673-76, 2001; Shen et al., Trends in Bio. Sci. 23:171-73, 1998; Kaiser et al. J. Biol. Chem. 274:21387-94, 1999; Ma et al., J. Biol. Chem. 275:24693-700, 2000; Allawi et al., J. Mol. Biol. 328:537-54, 2003; Sharma et al., J. Biol. Chem. 278:23487-96, 2003; and Feng et al., Nat. Struct. Mol. Biol. 11:450-56, 2004.

In particular embodiments, the reaction mix may contain reagents for assaying multiple (e.g., at least 2, 3, 4 or more) different targets sequences in parallel. In these cases, the reaction mix may contain multiple pairs of PCR primers, multiple different flap oligonucleotides having different flaps, and multiple different FRET cassettes for detecting the different flaps, once they are cleaved. In one embodiment, oligonucleotides in a mixture may have common flaps but different binding sequences to allow for, for example, any of a number of methylated cytosines to cleave a common FRET cassette and report a signal where a single fluorophore is indicative of the presence of a methylated cytosine. In this embodiment, which site is methylated in the sample may be determined after the presence of a methylated cytosine has identified. Optionally, the reaction may contain multiple invasive oligonucleotides if one of the PCR primers is not used as an invasive oligonucleotide. Upon cleavage of the FRET cassettes, multiple distinguishable fluorescent signals may be observed. The fluorophore may be selected from, e.g., 6-carboxyfluorescein (FAM), which has excitation and emission wavelengths of 485 nm and 520 nm respectively, Redmond Red, which has excitation and emission wavelengths of 578 nm and 650 nm respectively and Yakima Yellow, which has excitation and emission wavelengths of 532 nm and 569 nm respectively, and Quasor670 which has excitation and emission wavelengths of 644 nm and 670 nm respectively, although many others could be employed. In certain cases, at least one of the PCR primer pairs, flap oligonucleotides and FRET cassettes may be for the detection of an internal control. In such an assay, the control reagents may be, e.g., for amplification and detection of a locus that is not methylated or, for example, or for the amplification and detection of copies of the same locus. In these embodiments a reaction mixture may contain, in addition to other necessary reagents, at least an oligonucleotide having a 3' terminal nucleotide that base pairs with an A or T residue at a site of methylation, thereby providing for the detection of unmethylated copies of the genomic locus. These embodiments may also employ primers that amplified the unmethylated copies of the genomic locus.

As would be apparent, the various oligonucleotides used in the method are designed so as to not interfere with each other. For example, in particular embodiments, the flap oligonucleotide may be capped at its 3' end, thereby preventing its extension. Likewise, in certain embodiments the invasive oligonucleotide may also be capped at its 3' end if it not used as one of the PCR primers. In particular embodiment, if the invasive oligonucleotide is not used as one of the PCR primers, then the invasive oligonucleotide may be present at a concentration that is in the range of 5% to 50%, e.g., 10% to 40% of the concentration of the PCR primers. Further, in certain cases, the $T_m$s of the flap portion and the target complementary regions of the flap oligonucleotide may independently be at least 10° C. lower (e.g., 10-20° C. lower) than the $T_m$s of the PCR primers, which results in: a)

less hybridization of the flap oligonucleotide to the target nucleic acid at higher temperatures (65° C. to 75° C.) and b) less hybridization of any cleaved flap to the FRET cassette at higher temperatures (65° C. to 75° C.), thereby allowing the genomic locus to be amplified by PCR at a temperature at which the flap does not efficiently hybridize.

In a multiplex reaction, the primers may be designed to have similar thermodynamic properties, e.g., similar $T_m$s, G/C content, hairpin stability, and in certain embodiments may all be of a similar length, e.g., from 18 to 30 nt, e.g., 20 to 25 nt in length. The other reagents used in the reaction mixture may also be $T_m$ matched.

The assay mixture may be present in a vessel, including without limitation, a tube; a multi-well plate, such as a 96-well, a 384-well, a 1536-well plate; and a microfluidic device. In certain embodiments, multiple multiplex reactions are performed in the same reaction vessel. Depending on how the reaction is performed, the reaction mixture may be of a volume of 5 µl to 200 µl, e.g., 10 µl to 100 µl, although volumes outside of this range are envisioned.

In certain embodiments, a subject reaction mix may further contain a nucleic acid sample. In particular embodiments, the sample may contain genomic DNA or an amplified version thereof (e.g., genomic DNA amplified using the methods of Lage et al, Genome Res. 2003 13: 294-307 or published patent application US20040241658, for example). In exemplary embodiments, the genomic sample may contain genomic DNA from a mammalian cell, such as, a human, mouse, rat, or monkey cell. The sample may be made from cultured cells or cells of a clinical sample, e.g., a tissue biopsy, scrape or lavage or cells of a forensic sample (i.e., cells of a sample collected at a crime scene). In particular embodiments, the genomic sample may be from a formalin fixed paraffin embedded (FFPE) sample.

Method for Sample Analysis

In particular embodiments, the nucleic acid sample may be obtained from a biological sample such as cells, tissues, bodily fluids, and stool. Bodily fluids of interest include but are not limited to, blood, serum, plasma, saliva, mucous, phlegm, cerebral spinal fluid, pleural fluid, tears, lactal duct fluid, lymph, sputum, cerebrospinal fluid, synovial fluid, urine, amniotic fluid, and semen. In particular embodiments, a sample may be obtained from a subject, e.g., a human, and it may be processed prior to use in the subject assay. For example, the nucleic acid may be extracted from the sample prior to use, methods for which are known.

For example, DNA can be extracted from stool from any number of different methods, including those described in, e.g., Coll et al (J. of Clinical Microbiology 1989 27: 2245-2248), Sidransky et al (Science 1992 256: 102-105), Villa (Gastroenterology 1996 110: 1346-1353) and Nollau (Bio-Techniques 1996 20: 784-788), and U.S. Pat. Nos. 5,463,782, 7,005,266, 6,303,304 and 5,741,650. Commercial DNA extraction kits for the extraction of DNA from stool include the QIAamp stool mini kit (QIAGEN, Hilden, Germany), Instagene Matrix (Bio-Rad, Hercules, Calif.), and RapidPrep Micro Genomic DNA isolation kit (Pharmacia Biotech Inc., Piscataway, N.J.), among others.

Treatment of an initial nucleic acid sample to produce a treated nucleic acid sample involves contacting the initial nucleic acid sample with an agent that modifies unmethylated cytosine to uracil under conditions (e.g., a length of time and temperature, etc.) for the unmethylated cytosines in the nucleic acid to deaminated, thereby converting into uracils. Such methods are known and are described in, e.g., Clark et al (Nucleic Acids Res. 1994 22:2990-7), McDonald et al (Biotechniques. 1997 22: 272-4), Herman et al (Proc. Natl. Acad. Sci. 1996 93:9821-6) and Paul et al (Biotechniques 1996 21:126-33) as well as a variety of other references.

After treatment, the sample, referred to herein the "treated sample", is combined with other reagents to produce the reaction mixture described above, and then subjected to one or more sets of thermocycling conditions.

Exemplary conditions include, for example those described in Allawi et al (J Clin Microbiol. 2006 44: 3443-3447). In one embodiment, the reaction mixture may be subjected to conventional PCR thermocycling (i.e., multiple rounds of denaturation at a temperature of over 90° C., e.g., at about 95° C., annealing at a temperature of 65° C. to 75° C. and extension at a temperature of 65° C. to 75° C.) followed by a period at high temperature to denature the thermostable polymerase (e.g., about 99° C.), and then a period at a temperature that is about 10° C. below the extension temperature during which fluorescence is detected.

In other embodiments, the reaction mixture may be subject to cycling conditions in which an increase in the amount of amplified product (indicated by the amount of fluorescence) can be measured in real-time, where the term "real-time" is intended to refer to a measurement that is taken as the reaction progresses and products accumulate. The measurement may be expressed as an absolute number of copies or a relative amount when normalized to a control nucleic acid in the sample. In one real time embodiment, the reaction may be subjected to the thermocycling conditions described in, e.g., Tadokoro (J. Vir. Methods 2009 155: 182-186). In this embodiment, the reaction mixture may be subjected to multiple cycles of four steps that include a denaturation step at a temperature of over 90° C., e.g., at about 95° C., annealing at a temperature in the range of 61° C. to 69° C., flap cleavage at a temperature of 50° C., and extension at a temperature of 72° C. In this embodiment, fluorescence can be monitored in each cycle to provide a real time measurement of the amount of product that is accumulating in the reaction mixture.

In an alternative embodiment, the reaction mixture may be subjected to the following thermocycling conditions: a first set of 5 to 15 (e.g., 8 to 12) cycles of: i. a first temperature of at least 90° C.; ii. a second temperature in the range of 60° C. to 75° C. (e.g., 65° C. to 75° C.); iii. a third temperature in the range of 65° C. to 75° C.; followed by: a second set of 20-50 cycles of: i. a fourth temperature of at least 90° C.; ii. a fifth temperature that is at least 10° C. lower than the second temperature (e.g., in the range of 50° C. to 55° C.); and iii. a sixth temperature in the range of 65° C. to 75° C. No additional reagents need to be added to the reaction mixture during the thermocycling, e.g., between the first and second sets of cycles. In particular embodiments, the thermostable polymerase is not inactivated between the first and second sets of conditions, thereby allowing the target to be amplified during each cycle of the second set of cycles. In particular embodiments, the second and third temperatures are the same temperature such that "two step" thermocycling conditions are performed. Each of the cycles may be independently of a duration in the range of 10 seconds to 3 minutes, although durations outside of this range are readily employed. In each cycle of the second set of cycles (e.g., while the reaction is in the fifth temperature), a signal generated by cleavage of the flap probe may be measured to provide a real-time measurement of the amount of product in the sample.

Figure 2:
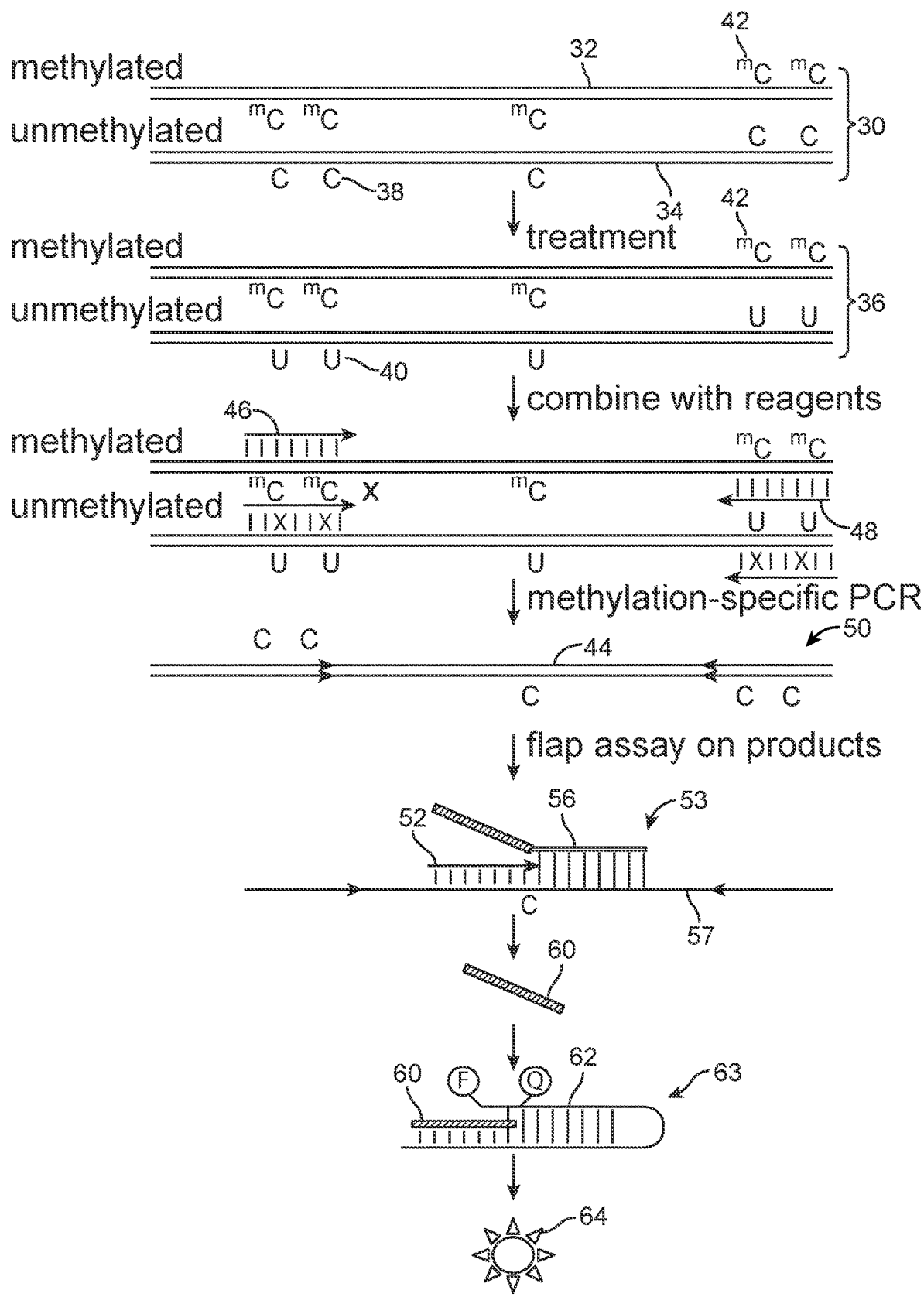
FIG. 2 schematically illustrates one embodiment of the subject method.

Some of the principles of an example of the subject method are schematically illustrated in FIG. 2. As noted above, however, the method may be performed in many different ways, e.g., by employing the first primer as an invasive oligonucleotide or by using a single methylation specific primer. As such, FIG. 2 shows an example of the method and should not be used to limit to only the embodiment shown.

With reference to FIG. 2, the method includes treating an initial sample 30 that comprises both methylated copies of a genomic locus 32 and unmethylated copies of the genomic locus 34 with an agent that modified unmethylated cytosine to uracil to produce treated sample 36. This treatment converts unmethylated cytosines, e.g., 38, to uracils e.g., 40. Methylated cytosines, e.g., 42 remain as methylated cytosines during the treatment. Treated sample 36 is then combined with the other reagents.

Product 44 is then amplified from treated sample 36 using first primer 46 and second primer 48, where the first primer hybridizes to a methylated sequence in the locus and the amplifying preferentially amplifies methylated copies of the genomic locus, to produce an amplified sample 50. As illustrated, both first primer 46 and the second primer 48 hybridize to methylated sequences. However, in practice, only one of the primers need hybridize to a methylated sequence. In particular embodiments and as noted above, the first primer may have a 3' terminal nucleotide that base pairs with a methylated cytosine, although this is not necessary if the reaction employs an invasive oligonucleotide that is distinct from the first primer. Such primers generally contain G nucleotides at sites of methylation, thereby allowing the primers to hybridize and extend more efficiently from sequences that contain methylated cytosine (which are not affected by the treatment) as opposed to sequences that contain unmethylated cytosine (which are converted to U's by the treatment). As illustrated in FIG. 2, the presence of product 44 in amplified sample 50 may be detected using a flap assay that employs invasive oligonucleotide 52 that has a 3' terminal nucleotide that base pairs with a G or C residue that corresponds to a site of methylation. The choice of the G or C residue is determined by whether the nucleotide that corresponds to the site of methylation to be detected is in the top or bottom strand of the amplification product. As shown, invasive oligonucleotide 52 has a terminal G nucleotide because it base pairs with a C corresponding to a site of methylation in initial sample 30. Again, as noted above, the embodiments illustrated in FIG. 2 employs a separate invasive oligonucleotide. In other embodiments, the first oligonucleotide may be employed as an invasive oligonucleotide in the method and, as such, there is no need to use a separate invasive oligonucleotide in the assay. As shown in FIG. 2, the 3' terminal nucleotide of the invasive oligonucleotide base pairs with an "internal" site of methylation in the sense that the site is within the amplified region and not part of the first and second primers.

As shown, the flap assay relies on the cleavage of complex 53 that contains an invasive oligonucleotide 52, flap oligonucleotide 56, and the bottom strand of product 44 by a flap endonuclease (not shown) to release flap 60. Released flap 60 then hybridizes to FRET cassette 62 to form a second complex 63 that is cleaved by the flap endonuclease to cleave the fluorophore from the complex and generate fluorescent signal 64 that can be measured to indicate the amount of product 44 in the amplified sample.

Certain aspects of the method described above are illustrated by example in FIGS. 3 and 4. FIG. 3 show the nucleotide sequences of methylated and unmethylated copies of a fragment of the human vimentin gene (VIM), before (SEQ ID NOS:1 and 2) and after bisulfite treatment (SEQ ID NOS: 3 and 4). FIG. 4 shows the nucleotide sequences of an exemplary forward primer, an exemplary reverse primer, and an exemplary flap oligonucleotide, aligned with the bisufite-treated fragment shown in FIG. 3.

The amount of product in the sample may be normalized relative to the amount of a control nucleic acid present in the sample, thereby determining a relative amount of the methylated copies of the genomic locus in the sample. In some embodiments, the control nucleic acid may be a different locus to the genomic locus and, in certain cases, may be detected using a flap assay that employs an invasive oligonucleotide having a 3' terminal nucleotide that base pairs with an A or T residue at the same site of methylation, thereby detecting the presence of unmethlyated copies of the genomic locus. The control may be measured in parallel with measuring the product in the same reaction mixture or a different reaction mix. If the control is measured in the same reaction mixture, the flap assay may include further reagents, particularly a second invasive oligonucleotide, a second flap probe having a second flap and a second FRET cassette that produces a signal that is distinguishable from the FRET cassette used to detect the product. In particular embodiments, the reaction mixture may further comprise PCR reagents and flap reagents for amplifying and determining the methylation state of another genomic locus that is known to be methylated in some samples.

In certain cases, fluorescence indicating the amount of cleaved flap can be detected by an automated fluorometer designed to perform real-time PCR having the following features: a light source for exciting the fluorophore of the FRET cassette, a system for heating and cooling reaction mixtures and a fluorometer for measuring fluorescence by the FRET cassette. This combination of features, allows real-time measurement of the cleaved flap, thereby allowing the amount of target nucleic acid in the sample to be quantified. Automated fluorometers for performing real-time PCR reactions are known in the art and can be adapted for use in this specific assay, for example, the ICYCLER™ from Bio-Rad Laboratories (Hercules, Calif.), the Mx3000P™, the MX3005P™ and the MX4000™ from Stratagene (La Jolla, Calif.), the ABI PRISM™ 7300, 7500, 7700, and 7900 Taq Man (Applied Biosystems, Foster City, Calif.), the SMARTCYCLER™, ROTORGENE 2000™ (Corbett Research, Sydney, Australia) and the GENE XPERT™ System (Cepheid, Sunnyvale, Calif.) and the LIGHTCYCLER™ (Roche Diagnostics Corp., Indianapolis, Ind.). The speed of ramping between the different reaction temperatures is not critical and, in certain embodiments, the default ramping speeds that are preset on thermocyclers may be employed.

In certain cases, the method may further involve graphing the amount of cleavage that occurs in several cycles, thereby providing a real time estimate of the abundance of the nucleic acid target. The estimate may be calculated by determining the threshold cycle (i.e., the cycle at which this fluorescence increases above a predetermined threshold; the "Ct" value or "Cp" value). This estimate can be compared to a control (which control may be assayed in the same reaction mix as the genomic locus of interest) to provide a normalized estimate. The thermocycler may also contain a software application for determining the threshold cycle for each of the samples. An exemplary method for determining the threshold cycle is set forth in, e.g., Luu-The et al (Biotechniques 2005 38: 287-293).

A device for performing sample analysis is also provided. In certain embodiments, the device comprises: a) a thermocycler programmed to perform the above-described method and b) a vessel comprising the above-described reaction mixture.

Utility

The method described finds use in a variety of applications, where such applications generally include sample analysis applications in which the presence of a methylated sequence in a given sample is detected.

In some embodiments, a biological sample may be obtained from a patient, and the sample may be analyzed using the method. In particular embodiments, the method may be employed to identify and/or estimate the amount of methylated copies of a genomic locus that are in a biological sample that contains both unmethylated copies of a genomic locus and methylated copies of the genomic locus In this example, the sample may contain at least 100 times (e.g., at least 1,000 times, at least 5,000 times, at least 10,000 times, at least 50,000 times or at least 100,000 times) more wild type copies of the genomic locus than mutant copies of the genomic locus.

In particular, the above-described methods may be employed to diagnose, to predict a response to treatment, or to investigate a cancerous condition or another mammalian disease that is associated with aberrant methylation including but not limited to: a) imprinting disorders including Beckwith-Wiedemann syndrome (associated with the BWS locus at 11p15.5), Prader-Willi syndrome (associated with an imprinted region at 15p11-q13), Angelman syndrome (also associated with an imprinted region at 15p11-q13), Albright hereditary osteodystrophy (associated with an imprinting at GNAS), pseudo-hypoparathyroidism types 1a and 1b (associated with imprinting at HYMAI, PLAG1 and ZAC-AS), transient neonatal diabetes mellitus and certain cancers (associated with the IGF2/H19 locus, the CDKN1C gene, DIRAS3 gene, and the MEST gene); b) repeat instability diseases including fragile X syndrome (associated with methylation at FRAXA) and facioscapulohumeral muscular dystrophy (associated with methylation at the FSHD locus); c) diseases caused by a defect in methylation pathways such as systemic lupus erythematosus, immunodeficiency (SLE, which is a result of global hypomethylation of T cells) and centromeric instability and facial anomalies syndrome (ICF) and d) other diseases such as alpha-thalassemia/mental retardation syndrome, X-linked (associated with abnormal methylation of ATRX). These diseases are reviewed in Robertson (DNA methylation and human disease Nat. Reviews 2005 6: 597-610). The method described above, may, for example, be used to identify aberrant methylation in an unborn child.

Hypermethylation of CpG islands in various loci is associated with various cancers. Without being bound to any particular theory, it is believed that methylation inactivates the expression of genes, including tumor suppressor genes, cell cycle related genes, DNA mismatch repair genes, hormone receptors and tissue or cell adhesion molecules. For example, tumor-specific deficiency of expression of the DNA repair genes MLH1 and MGMT and the tumor suppressors, p16, CDKN2 and MTS1, has been directly correlated to hypermethylation. Increased CpG island methylation is thought to result in the inactivation of these genes resulting in increased levels of genetic damage, predisposing cells to later genetic instability which then contributes to tumor progression.

Hypermethylation has been associated with several cancers, as illustrated in Table 1 (adapted from Das et al J. Clin. Oncol. 2004 22:4632-42). Thus, the method may be employed as a diagnostic for those cancers.

TABLE 1

| Methylated Gene | Putative Role in Tumor Development | Site of Tumor |
| --- | --- | --- |
| APC | Deranged regulation of cell proliferation, cell migration, cell adhesion, cytoskeletal reorganization, and chromosomal stability | Breast, Lung, Esophageal |
| BRCA1 | Implicated in DNA repair and transcription activation | Breast, Ovarian |
| CDKN2A/p16 | Cyclin-dependent kinase inhibitor | GIT, Head and neck, NHL, Lung |
| DAPK1 | Calcium/calmodulin-dependent enzyme that phosphorylates serine/threonine residues on proteins; Suppression of apoptosis | Lung |
| E-cadherin | Increasing proliferation, invasion, and/or metastasis | Breast, Thyroid, Gastric |
| ER | Hormone resistance | Breast, Prostate |
| GSTP1 | Loss of detoxification of active metabolites of several carcinogens | Prostate, Breast, Renal |
| hMLH1 | Defective DNA mismatch repair and gene mutations | Colon, Gastric, Endometrium, Ovarian |
| MGMT | p53-related gene involved in DNA repair and drug resistance | Lung, Brain |
| p15 | Unrestrained entry of cells into activation and proliferation | Leukemia, Lymphoma, Squamous cell carcinoma, lung |
| RASSF1A | Loss of negative regulator control of cell proliferation through inhibition of $G_1$/S-phase progression | Lung, Breast, Ovarian, Kidney, Nasopharyngeal |
| Rb | Failure to repress the transcription of cellular genes required for DNA replication and cell division | Retinoblastoma, Oligodendroglioma |
| VHL | Altered RNA stability through and erroneous degradation of RNA-bound proteins | Renal cell cancer |

Abbreviations: APC, adenomatous polyposis coli; BRCA1, breast cancer 1; CDKN2A/p16, cyclin-dependent kinase 2A; DAPK1, death-associated protein kinase 1; ER, estrogen receptor; GSTP1, glutathione S-transferase Pi 1; hMLH1, Mut L homologue 1; MGMT, O-6 methylguanine-DNA methyltransferase; RASSF1A, Ras association domain family member 1; Rb, retinoblastoma; VHL, von Hippel-Landau; GIT, gastrointestinal tract; NHL, non-Hodgkin's lymphoma.

The hypmermethylation of the following genes is also associated with cancer: PYCARD, CDH13, COX2, DAPK1, ESR1, GATA4, SYK, MLH1, TP73, PRDM2, PGR, SFRP1, SOCS1, SOCS3, STK11, TME1-1-2, THBS1, RASSF5, PRKCDBP, MGMT, CDKN2A, SFRP1, TME1-1-2, HS3ST2 (3OST2), RASSF1A, GATA4 and RARB.

In these embodiments, the method may be employed to detect aberrant methylation (e.g., hypermethylation or hypomethylation) in a gene, which aberrant methylation may be associated with, e.g., breast cancer, melanoma, renal cancer, endometrial cancer, ovarian cancer, pancreatic cancer, leukemia, colorectal cancer, prostate cancer, mesothelioma, glioma, medullobastoma, polycythemia, lymphoma, sarcoma or multiple myeloma, etc.

The use of DNA methylation markers for diagnosing cancers has been reviewed in a variety of publications such as: Qureshi et al (Int J Surg. 2010 Utility of DNA methylation markers for diagnosing cancer. 8:194-8), Muraki et al (Oncol Rep. 2009 Epigenetic DNA hypermethylation: clinical applications in endometrial cancer 22:967-72), Balch et al (Endocrinology. 2009 Minireview: epigenetic changes in ovarian cancer. 150:4003-11), Pfeifer (Semin Cancer Biol. 2009 DNA methylation patterns in lung carcinomas 19:181-7), Szalmás et al (Semin Cancer Biol. 2009 Epigenetic alterations in cervical carcinogenesis 19:144-52), Hoque (Expert Rev Mol Diagn. 2009 DNA methylation changes in prostate cancer: current developments and future clinical implementation 9:243-57), and Campan et al (Curr Top Microbiol Immunol. 2006 DNA methylation profiles of female steroid hormone-driven human malignancies 310: 141-78).

In one embodiment, the method may be employed to detected methylation in fecal DNA, thereby providing a diagnostic for colorectal cancer. In these embodiments, the method may be employed to investigate methylation of BMP3, EYA2, ALX4, or Vimentin, for example. These genes and their methylation are described in, for example, Chen et al (J Natl Cancer Inst. 2005 Detection in fecal DNA of colon cancer-specific methylation of the nonexpressed vimentin gene. 97:1124-32), Zou et al (Cancer Epidemiol Biomarkers Prev. 2007 Highly methylated genes in colorectal neoplasia: implications for screening. 16:2686-96) and Li (Nat Biotechnol. 2009 Sensitive digital quantification of DNA methylation in clinical samples. 27:858-63).

The subject method may be employed to diagnose patients with cancer or a pre-cancerous condition (e.g., adenoma etc.), alone, or in combination with other clinical techniques (e.g., a physical examination, such as, a colonoscopy) or molecular techniques (e.g., immunohistochemical analysis). For example, results obtained from the subject assay may be combined with other information, e.g., information regarding the methylation status of other loci, information regarding the mutations at other loci, information regarding rearrangements or substitutions in the same locus or at a different locus, cytogenetic information, information regarding rearrangements, gene expression information or information about the length of telomeres, to provide an overall diagnosis of cancer or other diseases.

In one embodiment, a sample may be collected from a patient at a first location, e.g., in a clinical setting such as in a hospital or at a doctor's office, and the sample may be forwarded to a second location, e.g., a laboratory where it is processed and the above-described method is performed to generate a report. A "report" as described herein, is an electronic or tangible document which includes report elements that provide test results that may include a Ct value, or Cp value, or the like that indicates the presence of mutant copies of the genomic locus in the sample. Once generated, the report may be forwarded to another location (which may the same location as the first location), where it may be interpreted by a health professional (e.g., a clinician, a laboratory technician, or a physician such as an oncologist, surgeon, pathologist), as part of a clinical diagnosis.

Kits

Also provided are kits for practicing the subject method, as described above. The components of the kit may be present in separate containers, or multiple components may be present in a single container. The components of the kit may include: a) a first primer and a second primer, where the first primer corresponds to a methylated sequence in the genomic locus and optionally contains a 3' terminal nucleotide that base pairs with a methylated cytosine or its complement in the methylated sequence; and b) flap assay reagents comprising a flap endonuclease, a FRET cassette and, if the first primer does not contain a 3' terminal nucleotide that base pairs with a methylated cytosine in the methylated sequence, an invasive oligonucleotide having a 3' terminal nucleotide that base pairs with a G or C residue that corresponds to a site of methylation in the genomic locus. The particulars of these reagents are described above. The kit may further contain an agent that modifies unmethylated cytosine to uracil. The kit further comprises PCR and flap reagents for amplification and detection of a control nucleic acid.

In addition to the above-mentioned components, the kit may further include instructions for using the components of the kit to practice the subject methods. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate. In addition to the instructions, the kits may also include one or more control samples, e.g., positive or negative controls analytes for use in testing the kit.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Example 1

Detection of Methylated C6ORF150 Sequences in the Presence of Unmethylated C6ORF150

The assay was designed to detect and quantitate the methylated CpG sequences in the presence of unmethylated sequence. In order to simulate the methylated and unmethylated genomic DNA, plasmids were prepared and cloned to match the sequence that results following the bisulfite reaction conversion of unmethylated C to U, which behaves as if it were a T in the PCR process, as exemplified for the vimentin sequence in FIG. 3. For each example, the methylated version of the sequence uses a plasmid with the CG motif intact and the unmethylated representative plasmid replaces this with a TG motif.

In this example, 2 CGs were designed on each primer, and they were not at 3'ends of the primers. The assay was then used to detect methylated copies spiked in unmethylated copies at 4 different levels, including $10^4$ methylated copies in $10^5$ unmethylated copies (1:10), $10^3$ methylated copies in $10^5$ unmethylated copies (1:100), $10^2$ methylated copies in $10^5$ unmethylated copies (1:1000), and 10 methylated copies in $10^5$ unmethylated copies (1:10000).

The target sequence of the plasmid representing the methylated sequence was as follows, with every C base corresponding to a methyl C for an analogous genomic DNA:

(SEQ ID NO: 1)
ATGGAATGTTAGGGGCGTTTCGATGGATTTTATCGAGTTTTCGGTTGTT

TTCGAGGTCGTTTTGTTTAAGGCGGGAAAGTTCGGTTTCGTTAGGAAGT

CGGGATTTCGGTAGAAAAAGAGCGTTTCGGATATTTAGGAGAGGTCGTT

CGTTCGCGTAATTGGGGTTCGCGTTAAAAAGGTTTTTTAGCGCGTTTAG

GATACGTAGTC

The assay employed a forward primer 5'-GGGATTCGGTAGAAAAAGAGCGT-3' (SEQ ID NO:2), a reverse primer 5'-ACCTTTTTAACGCGAACCCCA-3' (SEQ ID NO:3), an invasive oligonucleotide, that was not the forward PCR primer 5'-TCGGATATTTAG-GAGAGGTg-3' (SEQ ID NO:4), and a flap probe 5'-GACGCGGAGCGTTCGTTCGCG-3'/3C6/ (SEQ ID NO:5) where the area corresponding to methylated bases is shown underlined and the 3'-end is blocked with a hexanediol group in order to inhibit primer extension. The first nine bases of the flap probe are the region cleaved away by the flap endonuclease and then bind to the FRET cassette. Note that the 3'-end base of the invasive probe, shown as a lower case g, is designed to mismatch the target so as to discourage primer extension by the Taq polymerase. Primers, invasive oligos, and flap probes were supplied as non-catalog items by Integrated DNA Technologies (IDT, Coralville, Iowa).

The binding regions for the primers and invasive probe are shown on the target sequence underlined, and the target binding region of the flap probe is shown in italics:

(SEQ ID NO: 1)
ATGGAATGTTAGGGGCGTTTCGATGGATTTTATCGAGTTTTCGGTTGTT

TTCGAGGTCGTTTTGTTTAAGGCGGGAAAGTTCGGTTTCGTTAGGAAGT

CGGGATTTCGGTAGAAAAAGAGCGTTTCGGATATTTAGGAGAGGTCGTT

CGTTCGCGTAATTGGGGTTCGCGTTAAAAAGGTTTTTTAGCGCGTTTAG

GATACGTAGTC.

The FRET cassette used was 5'-FAM/TCT/Quencher/AGCCGGTTTTCCGGCTGAGACTCCGCGTCCGT-3'/3C6 (SEQ ID NO:6), where FAM is fluorescein, the quencher is the Eclipse® Dark Quencher, and the 3'-end is blocked with a hexanediol group in order to inhibit primer extension. The FRET cassette was supplied by Hologic (Madison, Wis.).

Cycling conditions were 95° C. for 3 min; 50 cycles at 95° C. for 20 sec, 50° C. for 1 min, and 70° C. for 30 sec, with a final 40° C. hold. Fluorescent signal acquisition was done at the 50° C. point in the cycle. The PCR reactions were done in LightCycler® 480 Multiwell 96 Plates (Roche, Indianapolis) in 10 mM MOPS pH 7.5, with 7.5 mM $MgCl_2$, and 250 µM dNTPs (Promega, Madison, Wis.). Taq polymerase was the iTaq enzyme (BioRad, Hercules, Calif.) and the cleavage enzyme was Cleavase 2.0 (Hologic, Madison, Wis.). Forward primer concentration was 500 nM, reverse primer concentration was 500 nM, flap probe was at 500 nM, invasive oligo probe was at 70 nM, and the FRET cassette was used at a final concentration of 200 nM. All amplification and detection was performed in the LightCycler 480 optical thermocycler (Roche, Indianapolis, Ind.).

Figure 5:
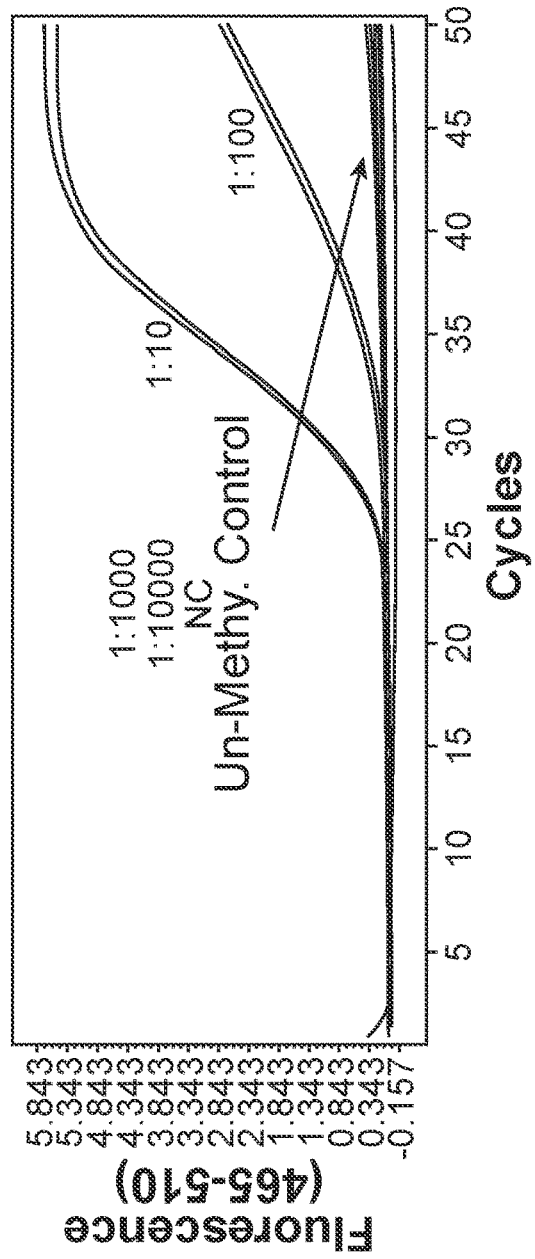
FIGS. 5 to 7 each provide data that is described in greater detail in the Examples section of this application.

Data showing kinetic amplification curves and the crossing point, Cp, of the different ratios of mutant to wild type in the amplification samples are shown in FIG. 5. In these assays, the Cp is calculated as being the point at which fluorescence rose to 18% of the maximum fluorescence.

The design of primers, invasive probe, and flap probe used in this example was unable to detect $10^2$ methylated copies in $10^5$ unmethylated copies (1:1000; FIG. 5). The reactions for detecting $10^3$ methylated copies in $10^5$ unmethylated copies (1:100) and $10^4$ methylated copies in $10^5$ unmethylated copies (1:10) were also suppressed by excessive amounts of unmethylated gene copies (FIG. 5).

Example 2

Detection of Methylated ZNF804B Sequences in the Presence of Unmethylated ZNF804B The assay was designed to detect and quantify the methylated CpG sequences of ZNF804B in the presence of unmethylated ZNF804B sequence. In order to simulate the methylated and unmethylated genomic DNA, plasmids were prepared and cloned to match the sequence that results following the bisulfite reaction conversion of unmethylated C to U, which behaves as if it were a T in the PCR process, as exemplified for the vimentin sequence in FIG. 3. For each example, the methylated version of the sequence uses a plasmid with the CG motif intact and the unmethylated representative plasmid replaces this with a TG motif.

In this example, 1 CG was designed on each primer, and they were not at 3'ends of the primers. The assay was then used to detect methylated copies spiked in unmethylated copies at 4 different levels, as in Example 1, including $10^4$ methylated copies in $10^5$ unmethylated copies (1:10), $10^3$ methylated copies in $10^5$ unmethylated copies (1:100), $10^2$ methylated copies in $10^5$ unmethylated copies (1:1000), and 10 methylated copies in $10^5$ unmethylated copies (1:10000).

The target sequence of the plasmid representing the methylated sequence was as follows, with every C base corresponding to a methyl C for an analogous genomic DNA:

(SEQ ID NO: 7)
TTAATTTGTTTGTTTTATTTGTGGTTGTATAGTTTATTTTTGTAATCGG
TTGGGGAGTTGTTGTTTTTGTTAACGTCGTCGTTAGTTAGAGCGTTGAA
GAAAAGTTGAAGGTTAGTAGGTAACGAAAGAGTAAAGA

The assay employed a forward primer 5'-GTGGTTGTATAGTTTATTTTTGTAATCGGT-3' (SEQ ID NO:8), a reverse primer 5'-ACCTTCAACTTTTCTT-CAACGCTC-3' (SEQ ID NO:9), an invasive oligonucleotide, that was not the forward PCR primer 5'-GG-GAGTTGTTGTTTTTGTTAAg-3' (SEQ ID NO:10), and a flap probe 5'-GACGCGGAGCGTCGTCGTTAG-3'/3C6/ (SEQ ID NO:11) where the area corresponding to methylated bases is shown underlined and the 3'-end is blocked with a hexanediol group in order to inhibit primer extension. The first nine bases of the flap probe are the region cleaved away by the flap endonuclease and then bind to the FRET cassette. Note that the 3'-end base of the invasive probe, shown as a lower case g, is designed to mismatch the target so as to discourage primer extension by the Taq polymerase. Primers, invasive oligos, and flap probes were supplied as non-catalog items by Integrated DNA Technologies (IDT, Coralville, Iowa).

The binding regions for the primers and invasive probe are shown on the target sequence underlined, and the target binding region of the flap probe is shown in italics:

(SEQ ID NO: 7)
TTAATTTGTTTGTTTTATTTGTGGTTGTATAGTTTATTTTTGTAATCGG
TTGGGGAGTTGTTGTTTTTGTTAACGTCGTCGTTAGTTAGAGCGTTGAA
GAAAAGTTGAAGGTTAGTAGGTAACGAAAGAGTAAAGA.

The FRET cassette used was 5'-FAM/TCT/Quencher/ AGCCGGTTTTCCGGCTGAGACTCCGCGTCCGT-3'/ 3C6 (SEQ ID NO:6), where FAM is fluorescein, the quencher is the Eclipse® Dark Quencher, and the 3'-end is blocked with a hexanediol group in order to inhibit primer extension. The FRET cassette was supplied by Hologic (Madison, Wis.).

Cycling conditions were 95° C. for 3 min; 50 cycles at 95° C. for 20 sec, 50° C. for 1 min, and 70° C. for 30 sec, with a final 40° C. hold. Fluorescent signal acquisition was done at the 50° C. point in the cycle. The PCR reactions were done in LightCycler® 480 Multiwell 96 Plates (Roche, Indianapolis) in 10 mM MOPS pH 7.5, with 7.5 mM $MgCl_2$, and 250 µM dNTPs (Promega, Madison, Wis.). Taq polymerase was the iTaq enzyme (BioRad, Hercules, Calif.) and the cleavage enzyme was Cleavase 2.0 (Hologic, Madison, Wis.). Forward primer concentration was 500 nM, reverse primer concentration was 500 nM, flap probe was at 500 nM, invasive oligo probe was at 70 nM, and the FRET cassette was used at a final concentration of 200 nM. All amplification and detection was performed in the LightCycler 480 optical thermocycler (Roche, Indianapolis, Ind.).

Figure 6:
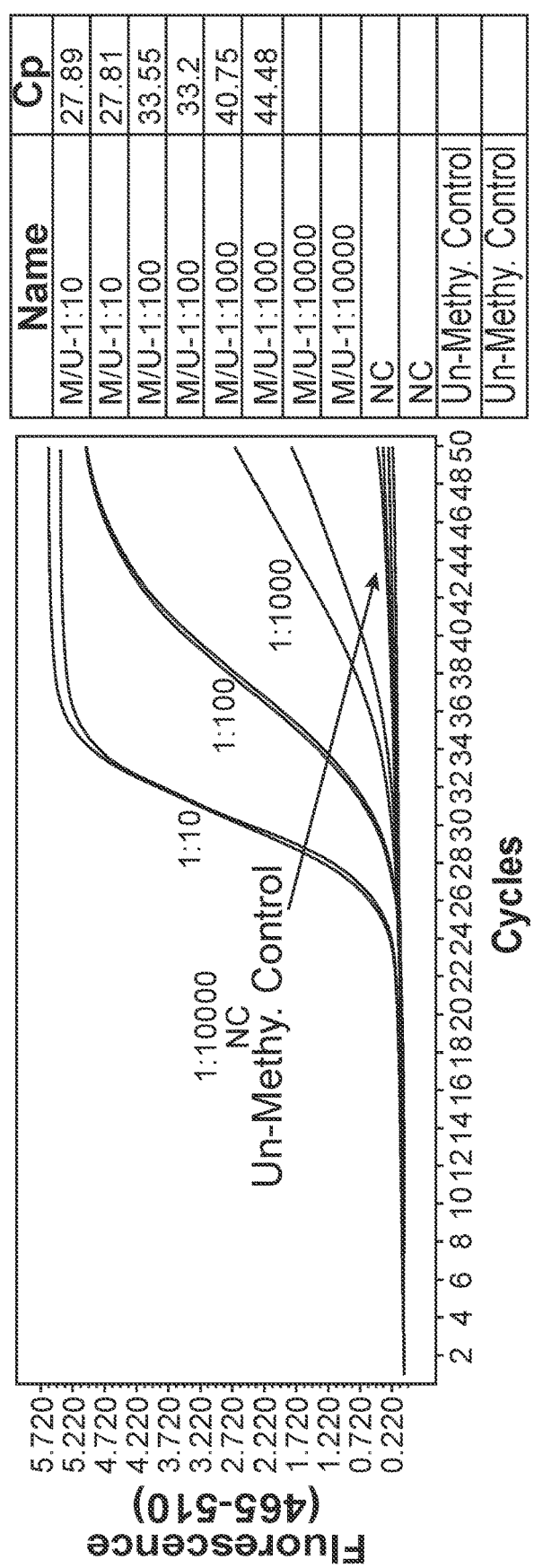

Data showing kinetic amplification curves and the crossing point, Cp, of the different ratios of mutant to wild type in the amplification samples are shown in FIG. 6. In these assays, the Cp is calculated as being the point at which fluorescence rose to 18% of the maximum fluorescence.

The design of primers, invasive probe, and flap probe used in this example could not detect 10 methylated copies in $10^5$ unmethylated copies (1:10000; FIG. 6). The reactions for detecting $10^2$ methylated copies in $10^5$ unmethylated copies (1:1000), $10^3$ methylated copies in $10^5$ unmethylated copies (1:100), and $10^4$ methylated copies in $10^5$ unmethylated copies (1:10) were also suppressed by excessive amounts of unmethylated gene copies (FIG. 6).

Example 3

Detection of Methylated Vimentin Sequences in the Presence of Unmethylated Vimentin The assay was designed to detect and quantitate the methylated CpG sequences of vimentin (VIM) in the presence of unmethylated VIM sequence. In order to simulate the methylated and unmethylated genomic DNA, plasmids were prepared and cloned to match the sequence that results following the bisulfite reaction conversion of unmethylated C to U, which behaves as if it were a T in the PCR process, as shown for the vimentin sequence in FIG. 3. The methylated version of the sequence uses a plasmid with the CG motif intact and the unmethylated representative plasmid replaces this with a TG motif.

In this example, 3 CGs were designed on each primer of the vimentin methylation detection assay, with one at the 3' end of the forward primer. In this assay, the forward primer is also the invasive oligonucleotide. There are also CG motifs located at the cleavage point of the flap probe, in both senses. The assay was then used to detect methylated copies spiked in unmethylated copies at 4 different levels, as in Example 1 and 2, including $10^4$ methylated copies in $10^5$ unmethylated copies (1:10), $10^3$ methylated copies in $10^5$ unmethylated copies (1:100), $10^2$ methylated copies in $10^5$ unmethylated copies (1:1000), and 10 methylated copies in $10^5$ unmethylated copies (1:10000).

The target sequence of the plasmid representing the methylated sequence was as follows, with every C base corresponding to a methyl C for an analogous genomic DNA:

(SEQ ID NO: 12)
TCGTGTTTTCGTTTTTTTATCGTAGGATGTTCGGCGGTTCGGGTATCGC
GAGTCGGTCGAGTTTTAGTCGGAGTTACGTGATTACGTTTATTCGTATT
TATAGTTTGGGCGACG

The assay employed a forward primer 5'-GGCGGTTCGGGTATCG-3' (SEQ ID NO:13), a reverse primer 5'-CGTAATCACGTAACTCCGACT-3' (SEQ ID NO:14), and a flap probe 5'-GACGCGGAGGCGAGT CGGTCG-3'/3C6/ (SEQ ID NO:15) where the area corresponding to methylated bases is shown underlined and the 3'-end is blocked with a hexanediol group in order to inhibit primer extension. The first nine bases of the flap probe are the region cleaved away by the flap endonuclease and then bind to the FRET cassette. Primers and flap probes were supplied as non-catalog items by Integrated DNA Technologies (IDT, Coralville, Iowa).

The binding regions for the primers and invasive probe are shown on the target sequence underlined, and the target binding region of the flap probe is shown in italics:

(SEQ ID NO: 12)
TCGTGTTTTCGTTTTTTTATCGTAGGATGTTCGGCGGTTCGGGTATCGC
GAGTCGGTCGAGTTTTAGTCGGAGTTACGTGATTACGTTTATTCGTATT
TATAGTTTGGGCGACG.

The FRET cassette used was 5'-FAM/TCT/Quencher/ AGCCGGTTTTCCGGCTGAGACTCCGCGTCCGT-3'/ 3C6 (SEQ ID NO:6), where FAM is fluorescein, the quencher is the Eclipse® Dark Quencher, and the 3'-end is blocked with a hexanediol group in order to inhibit primer extension. The FRET cassette was supplied by Hologic (Madison, Wis.).

Cycling conditions were 95° C. for 2 min; 45 cycles at 95° C. for 20 sec, 53° C. for 1 mi; and 40° C. to hold. Fluorescent signal acquisition was done at the 53° C. point in the cycle. The PCR reactions were done in LightCycler® 480 Multiwell 96 Plates (Roche, Indianapolis) in 10 mM MOPS pH 7.5, with 7.5 mM $MgCl_2$, and 250 µM dNTPs (Promega, Madison, Wis.). Taq polymerase was the HotStart GoTaq enzyme (Promega, Madison, Wis.) and the cleavage enzyme was Cleavase 2.0 (Hologic, Madison, Wis.). Forward primer concentration was 500 nM, reverse primer concentration was 500 nM, flap probe was at 500 nM, and the FRET cassette was used at a final concentration of 200 nM. All amplification and detection was performed in the LightCycler 480 optical thermocycler (Roche, Indianapolis, Ind.).

Figure 7:
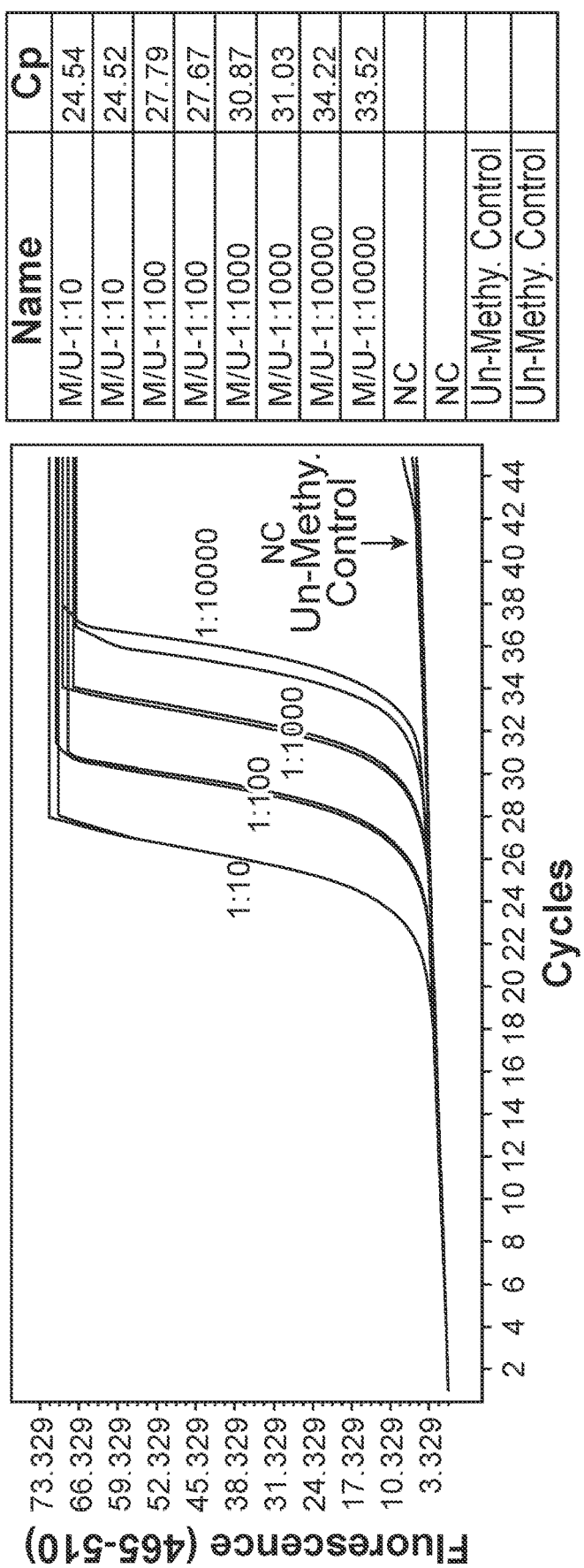

Data showing kinetic amplification curves and the crossing point, Cp, of the different ratios of mutant to wild type in the amplification samples are shown in FIG. 7. In these assays, the Cp is calculated as being the point at which fluorescence rose to 18% of the maximum fluorescence.

The design of primers, invasive probe, and flap probe used in this example could linearly detect down to 10 methylated copies in $10^5$ unmethylated copies (1:10000) and is clearly superior (FIG. 7) to the performance of Examples 1 and 2 (FIGS. 5 and 6).

What is claimed is:

1. A reaction mixture comprising:
   a) amplification reagents comprising a thermostable polymerase, nucleotides, a first primer and a second primer for amplifying a target genomic locus from a treated nucleic acid sample; wherein:
      i. said first primer hybridizes to a methylated sequence in said locus and contains a 3' terminal G or C nucleotide that corresponds to a methylated cytosine in said genomic locus; and
      ii. said reagents preferentially amplify methylated copies of said genomic locus, to produce an amplified sample;
   b) flap assay reagents comprising a flap endonuclease, a FRET cassette, and a flap oligonucleotide that comprises a G or C nucleotide at a position that corresponds to said methylated cytosine and wherein an invasive oligonucleotide distinct from the first primer is not included and wherein the first primer serves as an invasive oligonucleotide; and
   c) said treated nucleic acid sample, wherein said treated nucleic acid sample is made by treating an initial nucleic acid sample comprising both methylated copies and unmethylated copies of said genomic locus with an agent that modifies unmethylated cytosine to uracil;
   wherein said reaction mixture is characterized in that it can amplify and detect the presence of methylated copies of said genomic locus in said sample.

2. The reaction mixture of claim 1, wherein said flap oligonucleotide comprises an internal G or C nucleotide at a position that corresponds to a second methylated cytosine in said genomic locus.

3. The reaction mixture of claim 1, wherein said first primer comprises an internal G or C nucleotide at a position that corresponds to a second methylated cytosine in said genomic locus.

4. The reaction mixture of claim 1, wherein said first and second primers both hybridize to a methylated sequence in said genomic locus.

5. A kit comprising:
   a) PCR reagents that include a first primer and a second primer, where the first primer hybridizes to a methylated sequence in the genomic locus and contains a 3' terminal G or C nucleotide that corresponds to a methylated cytosine in the methylated sequence; and
   b) flap assay reagents comprising a flap endonuclease, a FRET cassette and a flap oligonucleotide that comprises a G or C nucleotide at a position that corresponds to said methylated cytosine and wherein an invasive oligonucleotide distinct from the first primer is not included and wherein the first primer serves as an invasive oligonucleotide.

6. The reaction mixture of claim 1, wherein the target genomic locus is Vimentin.

7. The reaction mixture of claim 6, wherein the methylated sequence in said locus comprises the nucleic acid sequence of SEQ ID NO:12.

8. The reaction mixture of claim 6, wherein the first primer comprises the sequence of SEQ ID NO:13.

9. The reaction mixture of claim 6, wherein the second primer comprises the sequence of SEQ ID NO:14.

10. The reaction mixture of claim 6, wherein the flap oligonucleotide comprises the sequence of SEQ ID NO:15.

11. The reaction mixture of claim 1, wherein
    the first primer comprises the sequence of SEQ ID NO:13,
    the second primer comprises the sequence of SEQ ID NO:14, and
    the flap oligonucleotide comprises the sequence of SEQ ID NO:15.

12. The kit of claim 5, wherein the methylated sequence is a methylated sequence to which the first primer hybridizes is a methylated sequence of Vimentin.

13. The kit of claim 12, wherein the methylated sequence in said locus comprises the nucleic acid sequence of SEQ ID NO:12.

14. The kit of claim 12, the first primer comprises the sequence of SEQ ID NO:13.

15. The kit of claim 12, wherein the second primer comprises the sequence of SEQ ID NO:14.

16. The kit of claim 12, wherein
    the first primer comprises the sequence of SEQ ID NO:13, and
    the second primer comprises the sequence of SEQ ID NO:14.

* * * * *

SEQUENCE LISTING

<160> NUMBER OF SEQ ID NOS: 19

<210> SEQ ID NO 1
<211> LENGTH: 207
<212> TYPE: DNA
<213> ORGANISM: Artificial Sequence
<220> FEATURE:
<223> OTHER INFORMATION: target methylated C6ORF150
<220> FEATURE:
<221> NAME/KEY: misc_difference
<222> LOCATION: 16, 21, 34, 42, 52, 58, 72, 82, 88, 99, 107, 121, 126,
      144, 148, 152, 154, 167, 169, 188, 190, 201, 207
<223> OTHER INFORMATION: methylated cytosine residues

<400> SEQUENCE: 1
atggaatgtt aggggcgttt cgatggattt tatcgagttt cggttgttt tcgaggtcgt       60 tttgtttaag gcgggaaagt tcggtttcgt taggaagtcg ggatttcggt agaaaaagag     120
cgtttcggat atttaggaga ggtcgttcgt tcgcgtaatt ggggttcgcg ttaaaaaggt     180
tttttagcgc gtttaggata cgtagtc                                         207

<210> SEQ ID NO 2
<211> LENGTH: 24
<212> TYPE: DNA
<213> ORGANISM: Artificial Sequence
<220> FEATURE:
<223> OTHER INFORMATION: Synthetic primer

<400> SEQUENCE: 2
gggatttcgg tagaaaaaga gcgt                                             24

<210> SEQ ID NO 3
<211> LENGTH: 21
<212> TYPE: DNA
<213> ORGANISM: Artificial Sequence
<220> FEATURE:
<223> OTHER INFORMATION: Synthetic primer

<400> SEQUENCE: 3
acctttttaa cgcgaacccc a                                                21

<210> SEQ ID NO 4
<211> LENGTH: 20
<212> TYPE: DNA
<213> ORGANISM: Artificial Sequence
<220> FEATURE:
<223> OTHER INFORMATION: Synthetic invasive oligonucleotide

<400> SEQUENCE: 4
tcggatattt aggagaggtg                                                  20

<210> SEQ ID NO 5
<211> LENGTH: 21
<212> TYPE: DNA
<213> ORGANISM: Artificial Sequence
<220> FEATURE:
<223> OTHER INFORMATION: Synthetic flap probe
<220> FEATURE:
<221> NAME/KEY: misc_difference
<222> LOCATION: 10, 14, 18, 20
<223> OTHER INFORMATION: Methylated cytosine
<220> FEATURE:
<221> NAME/KEY: misc_difference
<222> LOCATION: 21
<223> OTHER INFORMATION: 3'-C6 hexanediol modified

<400> SEQUENCE: 5

```
gacgcggagc gttcgttcgc g                                             21
```

<210> SEQ ID NO 6
<211> LENGTH: 35
<212> TYPE: DNA
<213> ORGANISM: Artificial Sequence
<220> FEATURE:
<223> OTHER INFORMATION: Synthetic  FRET cassette
<220> FEATURE:
<221> NAME/KEY: misc_difference
<222> LOCATION: 1
<223> OTHER INFORMATION: 5'-FAM modified
<220> FEATURE:
<221> NAME/KEY: misc_difference
<222> LOCATION: 3
<223> OTHER INFORMATION: Nucleotide modified with quencher
<220> FEATURE:
<221> NAME/KEY: misc_difference
<222> LOCATION: 35
<223> OTHER INFORMATION: 3'-C6 hexanediol modified

<400> SEQUENCE: 6

```
tctagccggt tttccggctg agactccgcg tccgt                              35
```

<210> SEQ ID NO 7
<211> LENGTH: 136
<212> TYPE: DNA
<213> ORGANISM: Artificial Sequence
<220> FEATURE:
<223> OTHER INFORMATION: Target ZNF804B sequence
<220> FEATURE:
<221> NAME/KEY: misc_difference
<222> LOCATION: 47, 74, 77, 80, 92, 123
<223> OTHER INFORMATION: Methylated cytosine

<400> SEQUENCE: 7

```
ttaatttgtt tgttttattt gtggttgtat agtttatttt tgtaatcggt tggggagttg   60 ttgttttttgt taacgtcgtc gttagttaga gcgttgaaga aaagttgaag gttagtaggt  120
aacgaaagag taaaga                                                  136
```

<210> SEQ ID NO 8
<211> LENGTH: 30
<212> TYPE: DNA
<213> ORGANISM: Artificial Sequence
<220> FEATURE:
<223> OTHER INFORMATION: Synthetic primer

<400> SEQUENCE: 8

```
gtggttgtat agtttatttt tgtaatcggt                                    30
```

<210> SEQ ID NO 9
<211> LENGTH: 24
<212> TYPE: DNA
<213> ORGANISM: Artificial Sequence
<220> FEATURE:
<223> OTHER INFORMATION: Synthetic primer

<400> SEQUENCE: 9

```
accttcaact tttcttcaac gctc                                          24
```

<210> SEQ ID NO 10
<211> LENGTH: 22
<212> TYPE: DNA
<213> ORGANISM: Artificial Sequence
<220> FEATURE:
<223> OTHER INFORMATION: Synthetic invasive oligonucleotide

<400> SEQUENCE: 10

```
gggagttgtt gtttttgtta ag                                              22

<210> SEQ ID NO 11
<211> LENGTH: 21
<212> TYPE: DNA
<213> ORGANISM: Artificial Sequence
<220> FEATURE:
<223> OTHER INFORMATION: Synthetic flap probe
<220> FEATURE:
<221> NAME/KEY: misc_difference
<222> LOCATION: 21
<223> OTHER INFORMATION: 3'-C6 hexanediol modified
<220> FEATURE:
<221> NAME/KEY: misc_difference
<222> LOCATION: 10, 13, 16
<223> OTHER INFORMATION: Methylated cytosine

<400> SEQUENCE: 11
gacgcggagc gtcgtcgtta g                                               21

<210> SEQ ID NO 12
<211> LENGTH: 114
<212> TYPE: DNA
<213> ORGANISM: Artificial Sequence
<220> FEATURE:
<223> OTHER INFORMATION: Target vimentin sequence
<220> FEATURE:
<221> NAME/KEY: misc_difference
<222> LOCATION: 2, 10, 21, 32, 35, 40, 47, 49, 54, 58, 69, 77, 85, 93,
      110, 113
<223> OTHER INFORMATION: Methylated cytosine

<400> SEQUENCE: 12
tcgtgttttc gttttttat cgtaggatgt tcggcggttc gggtatcgcg agtcggtcga      60
gttttagtcg gagttacgtg attacgttta ttcgtattta tagtttgggc gacg          114

<210> SEQ ID NO 13
<211> LENGTH: 16
<212> TYPE: DNA
<213> ORGANISM: Artificial Sequence
<220> FEATURE:
<223> OTHER INFORMATION: Synthetic primer

<400> SEQUENCE: 13
ggcggttcgg gtatcg                                                     16

<210> SEQ ID NO 14
<211> LENGTH: 21
<212> TYPE: DNA
<213> ORGANISM: Artificial Sequence
<220> FEATURE:
<223> OTHER INFORMATION: Synthetic primer

<400> SEQUENCE: 14
cgtaatcacg taactccgac t                                               21

<210> SEQ ID NO 15
<211> LENGTH: 21
<212> TYPE: DNA
<213> ORGANISM: Artificial Sequence
<220> FEATURE:
<223> OTHER INFORMATION: Synthetic flap probe
<220> FEATURE:
<221> NAME/KEY: misc_difference
<222> LOCATION: 11, 16, 20
<223> OTHER INFORMATION: Methylated cytosine
<220> FEATURE:
<221> NAME/KEY: misc_difference
```

```
<222> LOCATION: 21
<223> OTHER INFORMATION: 3'-C6 hexanediol modified

<400> SEQUENCE: 15
gacgcggagg cgagtcggtc g                                              21

<210> SEQ ID NO 16
<211> LENGTH: 100
<212> TYPE: DNA
<213> ORGANISM: Artificial Sequence
<220> FEATURE:
<223> OTHER INFORMATION: unmethylated vimentin fragment

<400> SEQUENCE: 16
ccgtgtcctc gtcctcctac cgcaggatgt tcggcggccc gggcaccgcg agccggccga    60
gctccagccg gagctacgtg actacgtcca cccgcaccta                         100

<210> SEQ ID NO 17
<211> LENGTH: 100
<212> TYPE: DNA
<213> ORGANISM: Artificial Sequence
<220> FEATURE:
<223> OTHER INFORMATION: Methylated vimentin fragment
<220> FEATURE:
<221> NAME/KEY: misc_difference
<222> LOCATION: 2, 10, 21, 32, 35, 40, 47, 49, 54, 58, 69, 77, 85, 93
<223> OTHER INFORMATION: Methylated cytosine

<400> SEQUENCE: 17
ccgtgtcctc gtcctcctac cgcaggatgt tcggcggccc gggcaccgcg agccggccga    60
gctccagccg gagctacgtg actacgtcca cccgcaccta                         100

<210> SEQ ID NO 18
<211> LENGTH: 100
<212> TYPE: DNA
<213> ORGANISM: Artificial Sequence
<220> FEATURE:
<223> OTHER INFORMATION: Unmethylated vimentin fragment after bisulfite
      reaction

<400> SEQUENCE: 18
uugtgtuutu gtuutuutau uguaggatgt tuggugguuu gggutauugug aguuggtuga    60 gutuuaguug gagutaugtg autaugtuua uuuguauuta                         100

<210> SEQ ID NO 19
<211> LENGTH: 100
<212> TYPE: DNA
<213> ORGANISM: Artificial Sequence
<220> FEATURE:
<223> OTHER INFORMATION: Methylated vimentin fragment after bisulfite
      reaction
<220> FEATURE:
<221> NAME/KEY: misc_difference
<222> LOCATION: 2, 10, 21, 32, 35, 40, 47, 49, 54, 58, 69, 77, 85, 93
<223> OTHER INFORMATION: Methylated cytosine

<400> SEQUENCE: 19
ucgtgtuutc gtuutuutau cguaggatgt tcggcgguuc ggguaucgcg agucggucga    60
gutuuagucg gagutacgtg autacgtuua uucguauuta                         100
```